US011851668B2

(12) United States Patent
Yan et al.

(10) Patent No.: US 11,851,668 B2
(45) Date of Patent: Dec. 26, 2023

(54) METHODS OF IDENTIFYING, SELECTING, AND PRODUCING SOUTHERN CORN RUST RESISTANT CROPS

(71) Applicants: HUAZHONG AGRICULTURAL UNIVERSITY, Wuhan (CN); PIONEER HI-BRED INTERNATIONAL, INC., Johnston, IA (US)

(72) Inventors: Jianbing Yan, Hubei (CN); Bailin Li, Johnston, IA (US); Girma M. Tabor, Johnston, IA (US); Gengshen Chen, Hubei (CN); Junqiang Ding, Hubei (CN); Zhibing Lai, Hubei (CN); Hongze Wang, Hubei (CN); Qianhui Yang, Hubei (CN)

(73) Assignees: HUAZHONG AGRICULTURAL UNIVERSITY, Wuhan (CN); PIONEER HI-BRED INTERNATIONAL, INC., Johnston, IA (US)

( * ) Notice: Subject to any disclaimer, the term of this patent is extended or adjusted under 35 U.S.C. 154(b) by 131 days.

(21) Appl. No.: 15/734,859

(22) PCT Filed: May 15, 2019

(86) PCT No.: PCT/US2019/032497
§ 371 (c)(1),
(2) Date: Dec. 3, 2020

(87) PCT Pub. No.: WO2019/236257
PCT Pub. Date: Dec. 12, 2019

(65) Prior Publication Data
US 2021/0230709 A1 Jul. 29, 2021

(30) Foreign Application Priority Data
Jun. 6, 2018 (WO) ................ PCT/CN2018/090067

(51) Int. Cl.
C12N 15/82 (2006.01)
C12Q 1/68 (2018.01)
C12Q 1/6895 (2018.01)

(52) U.S. Cl.
CPC ....... *C12N 15/8282* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2008/0016595 A1* 1/2008 Broglie .................... A01H 1/04
800/278

FOREIGN PATENT DOCUMENTS

| CN | 105861647 A | * | 8/2016 | ........... C12Q 1/6895 |
| CN | 106282394 | | 1/2017 | |
| WO | WO 2010/083178 | | 7/2010 | |
| WO | WO 2013/098819 | | 7/2013 | |
| WO | WO2013098819 | | 7/2013 | |
| WO | WO-2013098819 A1 | * | 7/2013 | ........... C07K 14/415 |
| WO | WO 2019/236257 | | 12/2019 | |

OTHER PUBLICATIONS

Sun et al., 2021, De novo transcriptome assembly, polymorphic SSR markers development and population genetics analyses for southern corn rust (Puccinia polysora). Scientific reports, 11(1), 1-11. (Year: 2021).*
Xiao et al., 2016, Genome-wide dissection of the maize ear genetic architecture using multiple populations. New Phytologist, 210(3), 1095-1106. (Year: 2016).*
PCT Search Report and Written Opinion prepared for PCT/US2019/032497, completed Jul. 16, 2019.
C. X. Chen et al., "Molecular tagging and genetic mapping of the disease resistance gene RppQ to southern corn rust", Theoretical and Applied Genetics ; International Journal of Plant Breeding Research, vol. 108, No. 5, Nov. 18, 2003 (Nov. 18, 2003), p. 945-950.
Wu Xiaojun et al., "Geographic and genetic identification of RppS, a novel locus conferring broad resistance to southern corn rust disease in China", Jan. 30, 2015 (Jan. 30, 2015), vol. 205, No. 1, p. 17-23.
Xiuping Wang et al: Gene expression profiles in *Maize* (L.) leaves inoculation with southern corn rust (Underw.), Acta Physiologiae Plantarum, Springer-Verlag, Berlin/Heidelberg, vol. 34, No. 3, Nov. 24, 2011 (Nov. 24, 2011), pp. 997-1006.
Chunjiang Zhou et al. Characterization and fine mapping of RppQ, a resistance gene to southern corn rust in maize , Molecular Genetics and Genomics, Springer, Berlin, DE, vol. 278, No. 6, Oct. 17, 2007 (Oct. 17, 2007), pp. 723-728.
Ya Zhang et al, Mapping of southern corn rust-resistant genes in the W2D inbred line of maize (*Zea mays* L.)11 , Molecular Breeding, Kluwer Academic Pub Li Shers, DO, vol. 25, No. 3, Oct. 8, 2009 (Oct. 8, 2009), pp. 433-439.
CN 106,282,394 A (China Golden Marker (Beijing) Biotech Col TD} 4 Jan. 20• 17 (Apr. 1, 2017) Especiaiiy Abstract; p. 2, para 5; p. 5, para 1-2; p. 15, para 10.
AC234• 175, Gen Bank Accession No. AC234175, *Zea mays* cultivar 873 chromosome 10 clone CH201-352E9, *** Sequencing in Progress ···, 22 unordered pieces, Sep. 13, 2014 (Online). [Retrieved on Jul. 7, 2020). f-1etrieved from the internet: < Uf-1L: 11ttps://v1,ww.ncbi.nlm.nih.gov/nuccore/AC234175>).

(Continued)

Primary Examiner — Cathy Kingdon Worley
Assistant Examiner — Santosh Sharma
(74) Attorney, Agent, or Firm — Barnes & Thornburg LLP

(57) ABSTRACT

The field is related to plant breeding and methods of identifying and selecting plants with resistance to southern corn rust. Provided are methods to identify novel genes that encode proteins providing plant resistance to southern corn rust and uses thereof. These disease resistant genes are useful in the production of resistant plants through breeding, transgenic modification, or genome editing.

12 Claims, 1 Drawing Sheet
Specification includes a Sequence Listing.

(56) References Cited

OTHER PUBLICATIONS

AC198651, Gen Bank Accession No. AC198651, *Zea mays* cultivar 873 chromosome 10 clone CH201-45H19,  ' Sequencing in Progress * , 11 unordered pieces, Sep. 23, 2020•13 [online]. [Retrieved on Jul. 7, 2020). f-1etrieved from the internet: <Uf-1L: 11ttps://ww.ncbi.nlm.nih.gov/nuccore/AC 198651 >).

* cited by examiner

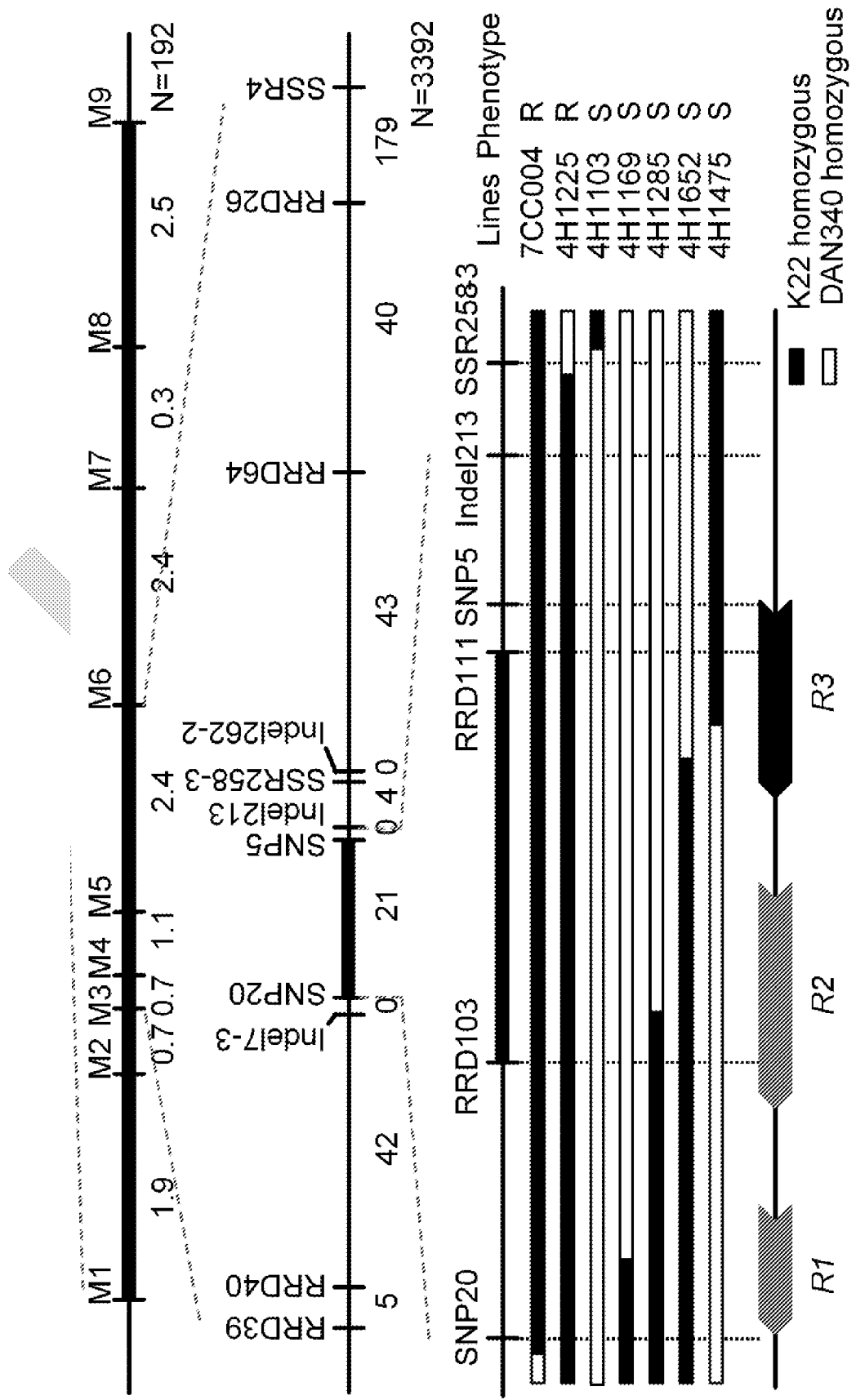

SEQUENCE LISTING

<160> NUMBER OF SEQ ID NOS: 44

<210> SEQ ID NO 1
<211> LENGTH: 62
<212> TYPE: DNA
<213> ORGANISM: Zea mays
<220> FEATURE:
<221> NAME/KEY: misc_feature
<222> LOCATION: (43)..(43)
<223> OTHER INFORMATION: n is a, c, g, or t

<400> SEQUENCE: 1
cacagaatct tacttccact caataatgat taatgaatgc ttngactggt tcgtatagcc    60
ga                                                                   62

<210> SEQ ID NO 2
<211> LENGTH: 57
<212> TYPE: DNA
<213> ORGANISM: Zea mays
<220> FEATURE:
<221> NAME/KEY: misc_feature
<222> LOCATION: (21)..(21)
<223> OTHER INFORMATION: n is a, c, g, or t

<400> SEQUENCE: 2
gacacttcag gggaacgtct ngcactgtcg ttcagagatg gaaacgaaat gtaccgt        57

<210> SEQ ID NO 3
<211> LENGTH: 42
<212> TYPE: DNA
<213> ORGANISM: Zea mays
<220> FEATURE:
<221> NAME/KEY: misc_feature
<222> LOCATION: (18)..(20)
<223> OTHER INFORMATION: n is a, c, g, or t

<400> SEQUENCE: 3
ttcacatgtg gttctgannn cttatgcagt gttggagcag tg                        42

<210> SEQ ID NO 4
<211> LENGTH: 62
<212> TYPE: DNA
<213> ORGANISM: Zea mays
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 4
catgtggttc tgaccgnnta ngcagtgttg gagcagtggc tggtgctgta cgtatccgct    60
ga                                                                   62

<210> SEQ ID NO 5
<211> LENGTH: 66
<212> TYPE: DNA
<213> ORGANISM: Zea mays
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (63)..(66)
<223> OTHER INFORMATION: n is a, c, g, or t

<400> SEQUENCE: 5

```
gctcgttggg tgcagatata ttataggtga gagtgagact agtgatgnng tggtggacga    60 atnnnn                                                                66
```

<210> SEQ ID NO 6
<211> LENGTH: 296
<212> TYPE: DNA
<213> ORGANISM: Zea mays
<220> FEATURE:
<221> NAME/KEY: misc_feature
<222> LOCATION: (201)..(201)
<223> OTHER INFORMATION: n is a, c, g, or t

<400> SEQUENCE: 6

```
aggatccaag aattatcatt agctgcacca gcgtctgcca gaatagagtg tacccactca    60
gcatcatgtt tgtcgccaac accaacactg ctcgcaacct ttctcaatct aattatctca   120
tttttatcag gtacctcgtc tggcaactgc aaggctaatc ctttgagcag agaatatatc   180
agaggcactt tctcttcaag nactgctccg acggcctcaa ccaacagccg acggaaagtt   240
attgcctgcc ctgcttgaat acagaggtca gccagtgttt cgaggtcaat aatttg       296
```

<210> SEQ ID NO 7
<211> LENGTH: 156
<212> TYPE: DNA
<213> ORGANISM: Zea mays
<220> FEATURE:
<221> NAME/KEY: misc_feature
<222> LOCATION: (127)..(127)
<223> OTHER INFORMATION: n is a, c, g, or t

<400> SEQUENCE: 7

```
caatcacctt gaccaattat atgcagcatt gccttctgac accaaaccct ccttcccagt    60
agacacagta gccttctcca agtgcttaat gtttatcgag gatcgtgaag atgtgactat   120
catcaanatt gacagccagt gcttacgcaa atcctg                             156
```

<210> SEQ ID NO 8
<211> LENGTH: 389
<212> TYPE: DNA
<213> ORGANISM: Zea mays
<220> FEATURE:
<221> NAME/KEY: misc_feature
<222> LOCATION: (143)..(143)
<223> OTHER INFORMATION: n is a, c, g, or t

<400> SEQUENCE: 8

```
aaatttgaac agaaattgta taatgttgtg tggatcaaca ggaaaacctt tgcatcaatc    60
tacacattac tgggcataga aaattgtatt aacaacaaga atgcagaagt tgtaggaaaa   120
ttaggtctat cttcataggt cantgagaat tctgtatatg atattaggtt gataacttac   180
agccaagtca gcggtaatgt caggaacact ttccccctga ggttttggaa tgttctccag   240
acaatggagg acttgctgaa aaaggccttt cagtgtcgca tctaggtcaa gagcaaccat   300
tcctggagta ccaagtaaga accgtattct tccagcactg gataacaaat atgataaggc   360
ataacctttt attgctgcaa agaggaaaa                                     389
```

<210> SEQ ID NO 9
<211> LENGTH: 71
<212> TYPE: DNA
<213> ORGANISM: Zea mays
<220> FEATURE:

```
<221> NAME/KEY: misc_feature
<222> LOCATION: (51)..(51)
<223> OTHER INFORMATION: n is a, c, g, or t

<400> SEQUENCE: 9
ggaaattttt tgacatcgt gatgcaaatt ttggggaaat ttggaaagac nccagctttc      60
caaaatgcat c                                                          71

<210> SEQ ID NO 10
<211> LENGTH: 55
<212> TYPE: DNA
<213> ORGANISM: Zea mays
<220> FEATURE:
<221> NAME/KEY: misc_feature
<222> LOCATION: (39)..(39)
<223> OTHER INFORMATION: n is a, c, g, or t

<400> SEQUENCE: 10
gagttccctc tgtttcttga cagccaggag acaacaagnt catcatatgc gatat          55

<210> SEQ ID NO 11
<211> LENGTH: 89
<212> TYPE: DNA
<213> ORGANISM: Zea mays
<220> FEATURE:
<221> NAME/KEY: misc_feature
<222> LOCATION: (23)..(23)
<223> OTHER INFORMATION: n is a, c, g, or t

<400> SEQUENCE: 11
ccatgtggaa tcaagaccac tgnttcaggc aattctataa tgcaactttg aattgatttc     60
gctgttttta ccaaaactct gaagaaatt                                        89

<210> SEQ ID NO 12
<211> LENGTH: 11437
<212> TYPE: DNA
<213> ORGANISM: Zea mays

<400> SEQUENCE: 12
ccgagtacat tgccgcagga cattgttgcg cgcaattgct ttggatgagg caaaccctgc     60
gggactacgg ttacaaatta accaaagtcc ctttgctatg tgataatgag agtgcaatta    120
agatggccga caatcccgtc gagcatagcc gcactaagca catagccatt cggtatcatt    180
ttcttaggga tcaccaacaa aaggggata tcgagatttc ttacattaat actaaagatc     240
aattagccga tatctttacc aagcctcttg atgaacaaac ttttaccaaa cttaggcatg    300
agctcaatat tcttgattct agaaatttct tttgctaagc ttgcacacat agctcatttg    360
aatacctttg atcatatctc ttttatatgc tatgactaat gtgttttcaa gtctatttca    420
aaccaagtca taggtatatt gaaagggaat tggagtcttc ggcgaagaca aaggcttcca    480
ctccgtaact catacttcgc caccactccg agcaactctc tcttctttgg gggagaaatg    540
agcatcaagg aaaaggactt catccttggg ggagagaata aaagctcaaa cgcaaaagga    600
cttcgtcttt ggtataatct taactcactt atttatgacc aaaggggaag aacttacttc    660
tagggctcta atgattccgt ttttttggcg attcatgcca aaaaggggga gaaatgagcc    720
caaagcaaaa ggaccgcacc accaccacca aattcaaaaa cttagtgctt tccaaaagtc    780
tttatcattt ggtatcctat tgtgttcaaa aggggagaa agtagtattt caaaaatggt    840
atatcaaaac cctcttgaac actaagaggt gaatctcttt tagggggagt tttgtttagt    900
caaaggaaaa gcatttgaaa caggggagg aaatttcaaa tcttaaaaaa tgcttttgca     960
```

```
aactcttatt tatttacctt tgactatctg caaaagatct atgaaaagga tttacaaaag    1020
gttttgcaaa aacaaaacaa gtggtgcaaa cgtggtccaa aatgttatat aagaaagaaa    1080
caattcatgc atattttgca agtatttata ttggcccaat ttcaagcaac ctttgcactt    1140
atattatgca aactagttca attatgcact tccatatttg ctttggtttg tgttggcatc    1200
aatcaccaaa aaggggagaa ttgaaaggga attaggctta cacctagttc ctaaatagtt    1260
ttggtggttg aatcgcccaa cacaaataaa ttgaactaac tagtttgctc tagattacat    1320
gttctacagg tgccaaaggt tcatctacaa ctatactaat tcgactgtcc ggaataccgt    1380
agattattcc ggacaggaga agcttttggg aaaaacaggc caagcgcgga ccgtccgggc    1440
tcttgcggcg gaccgtccgc aacatcggga tactcctcgg acagaaccaa tgcaaaaaca    1500
caagtttcca ctacagactg tccggaggaa aagcaaagac cgtccgagcc cttgcgcgga    1560
ccgtccggcc tctggcgcgg accgtccggt aggtgagaaa ccgaaaaacc cgaaggtaac    1620
gggttcggag aaatgaatta tagcggcctc gcggaccgtc cggaccaggc gggcggaccg    1680
tccgcgactg gctctgtctg acatctgacg acgcattaaa tgcaatatag ccgttgatat    1740
agccgttact gctgaccgtt gcattttcag ccgttgatct acagggcgg accgtccgca    1800 ccaggagggc ggaccgtccg cgctcagcag aatggcccaa cggctaggaa gtggttggtg    1860
gctataaata caaccccaac cacctccatt caatccatcc aagcattcca accttcaaca    1920
ttcaatacaa gagctagcaa tccattccaa gacacattca aagcctccat ctctccaagt    1980
ttcacaattg agaaaagaga tcattagtga ttagtagctt gagagagaaa gtgatccgtg    2040
tgttatttgt cgctcttgtt gcttggcttt ttaatcgtgc tttcttgatt cttttcattgc    2100 gatcaaactc acttgtaatt gaggcaagag acaccaatct tgtggtgatc cttgtaggaa    2160 cttttgtgttc caagtgattg agaaaagaaa gctcactcga tccgtggatc gtttgagaga    2220
gggaagggtt gaaagagacc cggcctttgt ggcctcctca acggggagta ggtttgcgag    2280
aaccgaacct cggtaaaaca aatccgcgtg tctcacttac ttattcgctt gcgatttgtt    2340
ttgcaccctc tctcgcggac tcatttatta ttactaacgc taacctcggc ttgtagttgt    2400
gattattttt gtaaatttca gtttcgccct attcaccccc ccctctaggc gactttcact    2460
caccagtatt gatttaagaa ctaagcgcct tgttattact ggtctatttg gataagtagg    2520
aatgacttag ttttttaataa tatttcaagt tttacttatc tgcaggtttt ttttccagag    2580
gtacacactg gcttagattc tgggctcaac tacaaaagga cgaagctgat ggagttttaa    2640
taaaggatgt ttgccgtcgc cgggaatcgg tggtcatgca attttgtgtt aattttggtt    2700
ggaggttttc taataggatt ccctttaat catcttggtg gttaaaaaaa aatcaaaaac    2760
ctttagtgtg ctatgtccct tcagagagca gtgtaatata acattttgtg ttgtctctaa    2820
tctattttga ggagaaagcc ggaactttt ctcgttatct gaaaaaatct ttggctagcc    2880
ttcgcgactc gccatctccc agccgtggcg ctctctcgcc cacgcacacc atgcagctgc    2940
ttcgtcattt ccagccatat gcgtgaagac atttgaattc gtccaccact gcatcactag    3000
tctcactctc acctataata tatctgcacc caacgagcag gtaccaagca attagcaaga    3060
gaaacacaag gtcgaggtgg tgaggcatgg agctcgcctt gggggccatg accagcttgg    3120
cccctaagct tggcgacctg ctcatggaga agtatgtcgt gcagaagggc ctcaagcccg    3180
acatcgagtc tctctccagg gagcttgtga tgatgaacgc cgctctcgtc gacgcgtccc    3240
gggttccacc tgaccagctc accgaggtgg aaaagctctg ggcacgcaag gtccgggact    3300
```

```
tgtcgtatga catggaggac gccgtcgacg atttcatcct gcgtgtggct ggtggtgacg   3360
actctgccgc cgactccaaa ttcttcaaga agacccttgc catggtcaag gacgtgatgt   3420
cgatgaagaa gttcaaggat cggtgccaga tctccgacaa ggtcaaagac atcaagaaac   3480
tctccaacga gttagctgaa cttcgtgcca agtacacggt aagggggtgtg ggtgctgatc   3540 tcgccgcgag caccggcatc gacacccgtg tcatcaatct gtacaagaaa gagacagatc   3600
tcgttggtat cgaggagtca agggacaaag tcattaggat gctgtctata ggggccaaag   3660
atgaagatgc acatgagttc catcaggatc taaagatagt gtctatagtc ggggttggag   3720
gactaggtaa gactactcta gccaaaacag tgcatgacat gcttaagaag caattcgact   3780
gttgtgcttt tatttctatt ggtagaactc ctaatctgaa taggacattc gagaagatgc   3840
tattggaact cgatcgtgag tataaacaag ttgacatggc cagatgggat ctagaacaat   3900
ttataaacga actggatgaa ttcttgaagg acaagaggta cgcccatgtc attcattctc   3960
cctctagttt agttgaattt tttcattcac tagtagagcg tgggcagttt tgccatgttt   4020
atatgcatac cgatttgcca agttattcat agctgtacac tcttgtgtca attttatata   4080
tatatatata tataggtact tgatcgttgt tgatgacata tgggatgttg actcatggga   4140
agcgatcaaa tatgccttaa aggacaatag ttgtggaagt agaataatca tgactactcg   4200
caattctggg tttgtcaaga aagtagaaga ggtttataga ttaaaacctc tttctaatga   4260
aaactccaag aaactgttct acaaaagaat agagagtcag gaaggagaaa gccttgatgg   4320
tgaactctct agtaaaatca tacataaatg tggcggcata ccattggcta tcattgcaat   4380
agctagtttg ttggttgaaa gatcaagtga ggagtggtca gaagtgtacg acaagattgg   4440
tcttgggaat gaggacaata caacaaagat aatgttatac agctactatg atctgcctcc   4500
ttatctcaag ccatgtctgc tgcaactaag catatatcca gaagactgtt tcattgatac   4560
aaaagctacc atatggaagt ggataggtga aggtctagtt catattgaga agaggaggg   4620 tagcctatt  aaggttggag aaagatactt caaggagctt gtgaatagaa gcatgatcca   4680
gccgatagag aacataaatg attggtttgt agaagagttc cgtattcacg acattgtgtt   4740
tgatctcatc tgtaagttgt ccaaggatga agacttcatt agccttagcg ggcaacattc   4800
atctcaggat agtttaagaa gagagaagaa aacaggtgtg cctcgctcag actgcaagct   4860
acgtcgtctg gtcgtccgaa atcaacgtgt gcagcgcttc cctgaagaaa ccatggacat   4920
gccagaggtg ttgagatcac ttagcattat agattgtaat attgcggttg tggccccaat   4980
tgatagcttc agggttttgcc gtgtgctgtc tatagtaaac aactacgtac ccatcagcct   5040
aaagcatctg gggaagctgt tgcatctcaa gttcctagag atagtataca cgcctattga   5100
tgagctccct aaggaaattg ggcatctgag gtctcttcag acactgatat tagtccgtac   5160
tggactagac gagctgccac cggctctttg ctcgcttaca cggctcatgt gtctgatagc   5220
ctatggcttc gaaaggttgc cagctgatag gatggggaac ctaacgtccc tggaggagct   5280
acaactaaat agggtagttg gccggagtgc cacccaagac ctagtggcag agtttggcaa   5340
gctgacgagg ttgagggtgg tcagcatcac cttttcagag cagctagagg agagcttgca   5400
agaagcattg gtgcaatctc tgtccaatct gcggcgactc caggaactag cttttgtg    5460 taaaatgcca gagcggggaa gcgatatgtg gggagactgg gagccaccaa ggcagctccg   5520
gcgcctgatt attgaaggca tcgacttctc acggcagcct cgatggatca accgctcctg   5580
cctgccacgc ctctgctcct tatatctgag ggtgcacgct cttgaagcac aggacctaga   5640
taatctagcg aggttgccag agctccagta cctccagcta tttggtctca gctttcctcc   5700
```

```
aaggtatact gttggcccag acgacttcag gaatctgagg ttctgcgaag tgggcacaac    5760
gttcgagttt cgtaagggcg ccatgccaag gcttgaagtg ctgcgatttg agtttatgc    5820 agggtactgg agttgggaag agaatggtgt gccgttcgag cagttcccaa cgaaggatgt    5880
gatcgaagat cttcacttgg acctggataa cgtccttta  cttcagcaag taatagtcaa    5940
agtcaactgc ttaggtgcta ctgccgcaca agtggaggag gtggaggccg tggtcatgcg    6000
tgccgtggaa aatcatgcca accgtccaac cataaaaatg gatcgagtat atgaagaaaa    6060
tatcttatct gatgaaaagt gggaggctct ggtgagtctg ctaaagaaaa tatgttttct    6120
tatatatatt tatatatata tatatatata tatttatgtt tgtgcacttc aattctcagc    6180
ttcggcgaca cattgaagag gattgctgcg tgcgcacgat gaaggataaa tctaatgctt    6240
tcttcatcag ccagctgtgg ttatatcgac atcttcagga agccattatt ttcatcgact    6300
gttcgggtgc cagcatgtgt gaggtgcaga aagtggaagc agcttataga catgcagccg    6360
aggttcatcc taaccatcca agtattgaac ttatcagaac aaacaccgac ggaatggcct    6420
cctcctcatc tgaccatccc aacacagagg ttcgtcctag ctgcgtggaa aattttttcag   6480 taattaatgg aaaccttagc tttgacggta aacttacca  ccaacgctta tttttcgttc    6540
ccaaactcca gcccaggaat tgatgactcg gtttgtcaga tccttcgacc cagcaccagc    6600
agcaggtacg tgtgcatgcc catgatctac actcttaaat taattttatt actctatcca    6660
gttatcacgt tccaatgcca tgtgtaagtt ttagtacctg tttatttttc gcttgcaatt    6720
gttgcatctt gaactcttgc ttctaacctc cattatttgt ctgtccactt caccaagaga    6780
cagaaaatca tagctctaac ttccatgaag cctaaacctc caaactcctt gggtctgttt    6840
agggcctccc accttgtcat gtgatacttc cttttcttgc tagttccata aaaagagatc    6900
tgattgagtc taacatctag aaattctcct cgtacaagtg atagaccccc actgtgttca    6960
taggaatgct tgacaggcag gattccatta cagtagatat cttccagaa  gatagatgtc    7020 cagactgcca agtacccaac ctcttctgag tcttgtcact gaatttcatc tgtgctttag    7080
tcactcatag gaatcttcaa atatttgata ggaaaaattt ccaccttgca acgaagaagt    7140
ttagctatcc tctctttctc ctgatcctca gccccaacaa cagaaactta acacttctca    7200
aagttgattt tcatccttga cattgcatca taacaagata aaataactct aatattgttc    7260
tggttacctt ttgagttctg taaaaaatgg ttgtatcatc atcatattgc aagtaactct    7320
gaaattaagc cctttagcgg acaacctctt ctagctctaa taaggcagat aaagcatctg    7380
tcactaagtt gaacaaaaaa gggaaaagag gatcccctgt ctgagacctt taaaacttct    7440
aaaatagtca cctctctcac cactcaaatc aataggtatc atgtcccact gaactgcctg    7500
tctggtccaa cctgtccata tattagaaaa aaaacatttt ctttgaagta cctcctccaa    7560
aaagttccaa ttcaccttat catatgccct ctaaaaaatc aagcttaaa  ataattccaa    7620 aaaccttat  agctcttagc tcatggagta catcttgcaa aagttgtctg gtatttgctt    7680
atcactttat ctgctgcaac tgttaacctc agattaagca tttcagtaag gatcttatag    7740
atcacattca gtaaacaaat aggcctatat tgtctagtag aggtggctgg cttgctctta    7800
ggaaatagga taataactcc atagttctag cttgcctgca ttgcatagca tttccttaac    7860
gtcaccacct atcagatgcc acaaaggctt aaatttttt  actgtaaatc catcaggacc    7920
aggagcggtg ttattcttca tgtagttttct ttctttttctt ttcttttgaa acatagtttc   7980
caaatatttt ttaagctact ttggttctca tttcagttag tagacgtcaa ggtttcatac    8040
```

```
aaaagctgat ttatagatta cttgcgttga atagctaacc aactaaaatg caccacgtat   8100
gctaatcaaa ccgatttcct tatggtaccc tgataaaaag cgtgctgttt ttttagaaaa   8160
taaatgttaa catgttaagt ggtttgatag gtcctaagat gattttaagt gaaaggaact   8220
aatcaaagca gcaaaagaaa gaaatatatc atatacctgg atggtagctc atgttttaat   8280
cttgtaaaag tgcttttact aaactgaatc gttttggatt agacatgttt attggctgtt   8340
gagtttgtga tccaaattct gaagaaggcg gccaagttgg cgagcgcgga tcgttttagg   8400
gtttcacctc tataaatatc tttgtaagcc gcaggagata tctatctcaa ttgtaaatct   8460
cttgcgatct gtaaccaccc gaaaatagtg agaagttgcc tgccggcgcc cgtggttttt   8520
tccccttcac tttggagggg ttttccacgt taaatccgtg tcttctctgt gattgatcct   8580
atttgtgtcg cattcattta taacattggc caaaaaaaac cttgtatcat tactgtttgc   8640
ttgaagaaat tctgtgattg cattttttcct ttacatgttt gctccatcct ttgcatttca   8700
acttatttac tatatacaca aaccaatatt tcaggtaaat gtgagttgct tcagtaccaa   8760
agagagaggt cctgttcagc aagatgatta gaagcattgg catggcttgt taattatatt   8820
tgtggttctt agtctaaaat cacattgaag agggagatgg acccaagtga tgcagttcat   8880
gtgttacctg tatctgtctc tattttataa gctgtcatat attttctcga aactatcttg   8940
tgtggatttt gtgtgaagtg tactttttagt ggcacaggcc atgtatttcc ttggaaacga   9000
ccatgagagt ttgtatatgg acttattttc cccccatttt ctttcctgag atgggctgtg   9060
tatttgcttg aaagataggg ttggtattat ctttgtattt gaactctaaa tgcttaaatg   9120
aagtgatcat cctggatgga gatatgtatg gtgtgaaccc tattctcgat gccaacgtgt   9180
gtgggatttt ggtgcgagct cctgtagctc gtctttgtta tatcgatggt gttcacaata   9240
tatgcaggtt catctaacac gaatgatgaa actatatgca ggcggtgccg gtcagcagag   9300
ggttgcctga cgcggagaag agatgcaggc tttgctggct ctggaggaat tcgaacgtgt   9360
ggcacacaca gatgtgaagc aaagatacaa tacaacaagg tcttccgtag ccagtagtag   9420
ccagtaggga agaagaagaa aaacgacccg agtttctcaa ggttgtcaag ctcaaaagtt   9480
agaaaaaggg tcaacggagc tgattcccctt cacaaaagtt acgtcagcaa taaattaccc   9540
cgttcattgc gaatggggtt agttaaaaaa agggtcaaca accaaaatta gcgtgcaaga   9600
ggagaaaact atgtagtata aaatgcgcat gagatcagaa gccacattaa tgcttctgtt   9660
gttacctaac aatcagggag gaaatttctg gaagttcaac tggtaggagg tgtgcatccg   9720
aaagataaag agcacagaac aaacgatcat aatttagacg aataagataa caacaaagct   9780
tttgcaacat agtatttgga caaggggttg aggcaaggag acccgctctc tcccattctt   9840
tttaatgtga tagtggatat gcttgctatt ctgattaata gagctaaagc agatggtcaa   9900
tttgacggtc tagtgccaca tttagtagat ggagggctct ctattttgca atatgcagat   9960
gacactttgt tgtttttttta taatgattta gagaaagcag caaatctgaa atcgcttctt  10020
gtagcctttg agcaagtatc cagtttgaaa attaattacc ataaaagtga gctattctgg  10080
caaggtgaaa atcataagaa gaaatacatg cttgctatat ggaatccttt gccaacctaa  10140
ggatcaaggg ggtaggtat taacaactta gatttacaaa ataaatgctt gctaagtaat  10200 tggttttttca agctagttaa tgaggatgga ctttggtaaa gtatgttgtg gaataaatac  10260
cttaagagac acaccttgtc aaaagtatcc ttcaggcggt gattctcatt tctgatcggg  10320
aattatgaaa gtgaaacatt tgtttttttta acctaggatc tttcatttta ggtaatagag  10380
aacaaataag attttgggag gacgtgtggt tgggagacca accactaatg aggcaatatc  10440
```

```
cttcactata tcatattgtg agacagaaaa gtaatattgt tgcgtctatc ttgagtacga    10500
cccctcaatg tttcgtttcg taggacgttg tgggtcagaa cataactttg tggtatgatc    10560
ttgttaatcg ggtggtgctc acctcgatga gctataatag agatgtcttt aagtggaggg    10620
taacatcttc acggtgcaat caatgtatca tattctaatt aataacggtc aaatgtttaa    10680
tcacaagctg atttggaaac taaatttacc ctaaagatta aaatcttttt gtggcatttg    10740
gttaaatgga tgttctaact aaggataacc taaccaaaac aaattcgaat gggaacaaaa    10800
aatgtgggtt ttgtaataca catgagtcta tttaacattt gtgtttagaa tgtaattttg    10860
ctcgccatat gtgaggttg tttcacttct gttttggtat gagtgtaccg aggtctgttc     10920
gtcatatttt tagtacgtgg ctcaccgcta ttgatttaag aactaagcgt cttgttatta    10980
catgtgtctc agtgttttgc tggactattt ggataagtag gaatgactta gtttttaata    11040
atgtttcaag ttttacttat ctgcagggtt tagattctgg gctcagccct cagctacaaa    11100
aagttgaagc tgatggagtt ttaataaaaa atgtttgtcg tcgcctggaa taggtggtca    11160
tgtaattttg tgttaatttt ggttagaggt tttctaatag tattactttg taataatctc    11220
ggtggtttta aaaaaaatca aaatatttta gtgtgatggt gtgtgactgt cccctcatag    11280
atcagtgtaa tataacaatt tgctaacctt ttttaggaga aagcagtaac ttttttctcca   11340 ttatctaaaa aaattctttg gctagccttc gcgagtcgcc gtctcccagc cgcacgctct    11400
ctcgcccacg cacacacgat tccttctcgc gctctcg                              11437

<210> SEQ ID NO 13
<211> LENGTH: 3129
<212> TYPE: DNA
<213> ORGANISM: Zea mays

<400> SEQUENCE: 13
atggagctcg ccttgggggc catgaccagc ttggcccccta agcttggcga cctgctcatg     60
gagaagtatg tcgtgcagaa gggcctcaag cccgacatcg agtctctctc cagggagctt    120
gtgatgatga cgccgctct cgtcgacgcg tcccgggttc cacctgacca gctcaccgag     180
gtggaaaagc tctgggcacg caaggtccgg gacttgtcgt atgacatgga ggacgccgtc    240
gacgatttca tcctgcgtgt ggctggtggt gacgactctg ccgccgactc caaattcttc    300
aagaagaccc ttgccatggt caaggacgtg atgtcgatga agaagttcaa ggatcggtgc    360
cagatctccg acaaggtcaa agacatcaag aaactctcca acgagttagc tgaacttcgt    420
gccaagtaca cggtaagggg tgtgggtgct gatctcgccg cgagcaccgg catcgacacc    480
cgtgtcatca atctgtacaa gaaagagaca gatctcgttg gtatcgagga gtcaagggac    540
aaagtcatta ggatgctgtc tatagggcc aaagatgaag atgcacatga gttccatcag    600
gatctaaaga tagtgtctat agtcggggtt ggaggactag gtaagactac tctagccaaa    660
acagtgcatg acatgcttaa gaagcaattc gactgttgtg cttttatttc tattggtaga    720
actcctaatc tgaataggac attcgagaag atgctattgg aactcgatcg tgagtataaa    780
caagttgaca tggccagatg ggatctagaa caatttataa acgaactgga tgaattcttg    840
aaggacaaga ggtacttgat cgttgttgat gacatatggg atgttgactc atgggaagcg    900
atcaaatatg ccttaaagga caatagttgt ggaagtagaa taatcatgac tactcgcaat    960
tctgggtttg tcaagaaagt agaagaggtt tatagattaa aacctctttc taatgaaaac   1020
tccaagaaac tgttctacaa aagaatagag agtcaggaag gagaaagcct tgatggtgaa    1080
```

-continued

```
ctctctagta aaatcataca taaatgtggc ggcataccat tggctatcat tgcaatagct    1140
agtttgttgg ttgaaagatc aagtgaggag tggtcagaag tgtacgacaa gattggtctt    1200
gggaatgagg acaatacaac aaagataatg ttatacagct actatgatct gcctccttat    1260
ctcaagccat gtctgctgca actaagcata tatccagaag actgtttcat tgatacaaaa    1320
gctaccatat ggaagtggat aggtgaaggt ctagttcata ttgagaaaga ggagggtagc    1380
ctatttaagg ttggagaaag atacttcaag gagcttgtga atagaagcat gatccagccg    1440
atagagaaca taaatgattg gtttgtagaa gagttccgta ttcacgacat tgtgtttgat    1500
ctcatctgta agttgtccaa ggatgaagac ttcattagcc ttagcgggca acattcatct    1560
caggatagtt taagaagaga aagaaaaca ggtgtgcctc gctcagactg caagctacgt     1620
cgtctggtcg tccgaaatca acgtgtgcag cgcttccctg aagaaccat ggacatgcca     1680 gaggtgttga gatcacttag cattatagat tgtaatattg cggttgtggc cccaattgat    1740
agcttcaggg tttgccgtgt gctgtctata gtaaacaact acgtaccat cagcctaaag     1800 catctgggga agctgttgca tctcaagttc ctagagatag tatacacgcc tattgatgag    1860
ctccctaagg aaattgggca tctgaggtct cttcagacac tgatattagt ccgtactgga    1920
ctagacgagc tgccaccggc tctttgctcg cttacacggc tcatgtgtct gatagcctat    1980
ggcttcgaaa ggttgccagc tgataggatg gggaacctaa cgtccctgga ggagctacaa    2040
ctaaataggg tagttggccg gagtgccacc caagacctag tggcagagtt tggcaagctg    2100
acgaggttga gggtggtcag catcaccttt tcagagcagc tagaggagag cttgcaagaa    2160
gcattggtgc aatctctgtc caatctgcgg cgactccagg aactagagct tttgtgtaaa    2220
atgccagagc ggggaagcga tatgtgggga gactgggagc caccaaggca gctccggcgc    2280
ctgattattg aaggcatcga cttctcacgg cagcctcgat ggatcaaccg ctcctgcctg    2340
ccacgcctct gctccttata tctgagggtg cacgctcttg aagcacagga cctagataat    2400
ctagcgaggt tgccagagct ccagtacctc cagctatttg gtctcagctt tcctccaagg    2460
tatactgttg gcccagacga cttcaggaat ctgaggttct gcgaagtggg cacaacgttc    2520
gagtttcgta agggcgccat gccaaggctt gaagtgctgc gatttggagt ttatgcaggg    2580
tactggagtt gggaagagaa tggtgtgccg ttcgagcagt tcccaacgaa ggatgtgatc    2640
gaagatcttc acttggacct ggataacgtc cttttacttc agcaagtaat agtcaaagtc    2700
aactgcttag gtgctactgc cgcacaagtg gaggaggtgg aggccgtggt catgcgtgcc    2760
gtggaaaatc atgccaaccg tccaaccata aaaatggatc gagtatatga agaaaatatc    2820
ttatctgatg aaaagtggga ggctctgctt cggcgacaca ttgaagagga ttgctgcgtg    2880
cgcacgatga aggataaatc taatgctttc ttcatcagcc agctgtggtt atatcgacat    2940
cttcaggaag ccattatttt catcgactgt tcgggtgcca gcatgtgtga ggtgcagaaa    3000
gtggaagcag cttatagaca tgcagccgag gttcatccta accatccaag tattgaactt    3060
atcagaacaa acaccgacgg aatggcctcc tcctcatctg accatcccaa cacagagccc    3120
aggaattga                                                           3129
```

<210> SEQ ID NO 14
<211> LENGTH: 1042
<212> TYPE: PRT
<213> ORGANISM: Zea mays

<400> SEQUENCE: 14

Met Glu Leu Ala Leu Gly Ala Met Thr Ser Leu Ala Pro Lys Leu Gly

-continued

```
1               5                   10                  15
Asp Leu Leu Met Glu Lys Tyr Val Val Gln Lys Gly Leu Lys Pro Asp
                20                  25                  30

Ile Glu Ser Leu Ser Arg Glu Leu Val Met Met Asn Ala Ala Leu Val
                35                  40                  45

Asp Ala Ser Arg Val Pro Pro Asp Gln Leu Thr Glu Val Glu Lys Leu
    50                  55                  60

Trp Ala Arg Lys Val Arg Asp Leu Ser Tyr Asp Met Glu Asp Ala Val
65                  70                  75                  80

Asp Asp Phe Ile Leu Arg Val Ala Gly Asp Asp Ser Ala Ala Asp
                85                  90                  95

Ser Lys Phe Phe Lys Lys Thr Leu Ala Met Val Lys Asp Val Met Ser
                100                 105                 110

Met Lys Lys Phe Lys Asp Arg Cys Gln Ile Ser Asp Lys Val Lys Asp
                115                 120                 125

Ile Lys Lys Leu Ser Asn Glu Leu Ala Glu Leu Arg Ala Lys Tyr Thr
        130                 135                 140

Val Arg Gly Val Gly Ala Asp Leu Ala Ala Ser Thr Gly Ile Asp Thr
145                 150                 155                 160

Arg Val Ile Asn Leu Tyr Lys Lys Glu Thr Asp Leu Val Gly Ile Glu
                165                 170                 175

Glu Ser Arg Asp Lys Val Ile Arg Met Leu Ser Ile Gly Ala Lys Asp
            180                 185                 190

Glu Asp Ala His Glu Phe His Gln Asp Leu Lys Ile Val Ser Ile Val
            195                 200                 205

Gly Val Gly Gly Leu Gly Lys Thr Thr Leu Ala Lys Thr Val His Asp
    210                 215                 220

Met Leu Lys Lys Gln Phe Asp Cys Cys Ala Phe Ile Ser Ile Gly Arg
225                 230                 235                 240

Thr Pro Asn Leu Asn Arg Thr Phe Glu Lys Met Leu Leu Glu Leu Asp
                245                 250                 255

Arg Glu Tyr Lys Gln Val Asp Met Ala Arg Trp Asp Leu Glu Gln Phe
            260                 265                 270

Ile Asn Glu Leu Asp Glu Phe Leu Lys Asp Lys Arg Tyr Leu Ile Val
            275                 280                 285

Val Asp Asp Ile Trp Asp Val Asp Ser Trp Glu Ala Ile Lys Tyr Ala
        290                 295                 300

Leu Lys Asp Asn Ser Cys Gly Ser Arg Ile Ile Met Thr Thr Arg Asn
305                 310                 315                 320

Ser Gly Phe Val Lys Lys Val Glu Glu Val Tyr Arg Leu Lys Pro Leu
                325                 330                 335

Ser Asn Glu Asn Ser Lys Lys Leu Phe Tyr Lys Arg Ile Glu Ser Gln
            340                 345                 350

Glu Gly Glu Ser Leu Asp Gly Glu Leu Ser Ser Lys Ile Ile His Lys
            355                 360                 365

Cys Gly Gly Ile Pro Leu Ala Ile Ala Ile Ala Ser Leu Leu Val
    370                 375                 380

Glu Arg Ser Ser Glu Glu Trp Ser Glu Val Tyr Asp Lys Ile Gly Leu
385                 390                 395                 400

Gly Asn Glu Asp Asn Thr Thr Lys Ile Met Leu Tyr Ser Tyr Asp
                405                 410                 415

Leu Pro Pro Tyr Leu Lys Pro Cys Leu Leu Gln Leu Ser Ile Tyr Pro
                420                 425                 430
```

```
Glu Asp Cys Phe Ile Asp Thr Lys Ala Thr Ile Trp Lys Trp Ile Gly
        435                 440                 445

Glu Gly Leu Val His Ile Glu Lys Glu Gly Ser Leu Phe Lys Val
450                 455                 460

Gly Glu Arg Tyr Phe Lys Glu Leu Val Asn Arg Ser Met Ile Gln Pro
465                 470                 475                 480

Ile Glu Asn Ile Asn Asp Trp Phe Val Glu Glu Phe Arg Ile His Asp
                485                 490                 495

Ile Val Phe Asp Leu Ile Cys Lys Leu Ser Lys Asp Glu Asp Phe Ile
                500                 505                 510

Ser Leu Ser Gly Gln His Ser Ser Gln Asp Ser Leu Arg Arg Glu Lys
                515                 520                 525

Lys Thr Gly Val Pro Arg Ser Asp Cys Lys Leu Arg Arg Leu Val Val
530                 535                 540

Arg Asn Gln Arg Val Gln Arg Phe Pro Glu Glu Thr Met Asp Met Pro
545                 550                 555                 560

Glu Val Leu Arg Ser Leu Ser Ile Ile Asp Cys Asn Ile Ala Val Val
                565                 570                 575

Ala Pro Ile Asp Ser Phe Arg Val Cys Arg Val Leu Ser Ile Val Asn
                580                 585                 590

Asn Tyr Val Pro Ile Ser Leu Lys His Leu Gly Lys Leu Leu His Leu
                595                 600                 605

Lys Phe Leu Glu Ile Val Tyr Thr Pro Ile Asp Glu Leu Pro Lys Glu
610                 615                 620

Ile Gly His Leu Arg Ser Leu Gln Thr Leu Ile Leu Val Arg Thr Gly
625                 630                 635                 640

Leu Asp Glu Leu Pro Pro Ala Leu Cys Ser Leu Thr Arg Leu Met Cys
                645                 650                 655

Leu Ile Ala Tyr Gly Phe Glu Arg Leu Pro Ala Asp Arg Met Gly Asn
                660                 665                 670

Leu Thr Ser Leu Glu Glu Leu Gln Leu Asn Arg Val Val Gly Arg Ser
                675                 680                 685

Ala Thr Gln Asp Leu Val Ala Glu Phe Gly Lys Leu Thr Arg Leu Arg
                690                 695                 700

Val Val Ser Ile Thr Phe Ser Glu Gln Leu Glu Glu Ser Leu Gln Glu
705                 710                 715                 720

Ala Leu Val Gln Ser Leu Ser Asn Leu Arg Arg Leu Gln Glu Leu Glu
                725                 730                 735

Leu Leu Cys Lys Met Pro Glu Arg Gly Ser Asp Met Trp Gly Asp Trp
                740                 745                 750

Glu Pro Pro Arg Gln Leu Arg Arg Leu Ile Ile Glu Gly Ile Asp Phe
                755                 760                 765

Ser Arg Gln Pro Arg Trp Ile Asn Arg Ser Cys Leu Pro Arg Leu Cys
                770                 775                 780

Ser Leu Tyr Leu Arg Val His Ala Leu Glu Ala Gln Asp Leu Asp Asn
785                 790                 795                 800

Leu Ala Arg Leu Pro Glu Leu Gln Tyr Leu Gln Leu Phe Gly Leu Ser
                805                 810                 815

Phe Pro Pro Arg Tyr Thr Val Gly Pro Asp Asp Phe Arg Asn Leu Arg
                820                 825                 830

Phe Cys Glu Val Gly Thr Thr Phe Glu Phe Arg Lys Gly Ala Met Pro
                835                 840                 845
```

-continued

```
Arg Leu Glu Val Leu Arg Phe Gly Val Tyr Ala Gly Tyr Trp Ser Trp
    850                 855                 860

Glu Glu Asn Gly Val Pro Phe Glu Gln Phe Pro Thr Lys Asp Val Ile
865                 870                 875                 880

Glu Asp Leu His Leu Asp Leu Asp Asn Val Leu Leu Leu Gln Gln Val
                885                 890                 895

Ile Val Lys Val Asn Cys Leu Gly Ala Thr Ala Ala Gln Val Glu Glu
            900                 905                 910

Val Glu Ala Val Val Met Arg Ala Val Glu Asn His Ala Asn Arg Pro
        915                 920                 925

Thr Ile Lys Met Asp Arg Val Tyr Glu Glu Asn Ile Leu Ser Asp Glu
    930                 935                 940

Lys Trp Glu Ala Leu Leu Arg Arg His Ile Glu Glu Asp Cys Cys Val
945                 950                 955                 960

Arg Thr Met Lys Asp Lys Ser Asn Ala Phe Phe Ile Ser Gln Leu Trp
                965                 970                 975

Leu Tyr Arg His Leu Gln Glu Ala Ile Ile Phe Ile Asp Cys Ser Gly
                980                 985                 990

Ala Ser Met Cys Glu Val Gln Lys  Val Glu Ala Ala Tyr  Arg His Ala
            995                 1000                1005

Ala Glu  Val His Pro Asn His  Pro Ser Ile Glu Leu  Ile Arg Thr
    1010                1015                1020

Asn Thr Asp Gly Met Ala Ser  Ser Ser Ser Asp His  Pro Asn Thr
    1025                1030                1035

Glu Pro  Arg Asn
    1040

<210> SEQ ID NO 15
<211> LENGTH: 20
<212> TYPE: DNA
<213> ORGANISM: Zea mays

<400> SEQUENCE: 15
ggaaagcctg agtgctggaa                                                 20

<210> SEQ ID NO 16
<211> LENGTH: 20
<212> TYPE: DNA
<213> ORGANISM: Zea mays

<400> SEQUENCE: 16
ccgctgactt ggctgtaagt                                                 20

<210> SEQ ID NO 17
<211> LENGTH: 20
<212> TYPE: DNA
<213> ORGANISM: Zea mays

<400> SEQUENCE: 17
agttcagggc agttcaccac                                                 20

<210> SEQ ID NO 18
<211> LENGTH: 20
<212> TYPE: DNA
<213> ORGANISM: Zea mays

<400> SEQUENCE: 18
taacggcttg gcccaactac                                                 20
```

```
<210> SEQ ID NO 19
<211> LENGTH: 25
<212> TYPE: DNA
<213> ORGANISM: Zea mays

<400> SEQUENCE: 19
gttcattcgt ttctaataca gtggc                                   25

<210> SEQ ID NO 20
<211> LENGTH: 25
<212> TYPE: DNA
<213> ORGANISM: Zea mays

<400> SEQUENCE: 20
gttcattcgt ttctaataca gtggc                                   25

<210> SEQ ID NO 21
<211> LENGTH: 20
<212> TYPE: DNA
<213> ORGANISM: Zea mays

<400> SEQUENCE: 21
ggctggttgc gctaaaatag                                         20

<210> SEQ ID NO 22
<211> LENGTH: 20
<212> TYPE: DNA
<213> ORGANISM: Zea mays

<400> SEQUENCE: 22
tttttcgctt gcatttgttg                                         20

<210> SEQ ID NO 23
<211> LENGTH: 23
<212> TYPE: DNA
<213> ORGANISM: Zea mays

<400> SEQUENCE: 23
tcatcatccc atatgtcatc aac                                     23

<210> SEQ ID NO 24
<211> LENGTH: 23
<212> TYPE: DNA
<213> ORGANISM: Zea mays

<400> SEQUENCE: 24
ggcagttttg ccatgtttat atg                                     23

<210> SEQ ID NO 25
<211> LENGTH: 20
<212> TYPE: DNA
<213> ORGANISM: Zea mays

<400> SEQUENCE: 25
aggagccaag atcctaccgt                                         20

<210> SEQ ID NO 26
<211> LENGTH: 20
<212> TYPE: DNA
<213> ORGANISM: Zea mays

<400> SEQUENCE: 26
catttagggc cggtgagaca                                         20
```

<210> SEQ ID NO 27
<211> LENGTH: 20
<212> TYPE: DNA
<213> ORGANISM: Zea mays

<400> SEQUENCE: 27
agatggcgat agctgcatgg                                               20

<210> SEQ ID NO 28
<211> LENGTH: 20
<212> TYPE: DNA
<213> ORGANISM: Zea mays

<400> SEQUENCE: 28
gcgcccacgg tatacatcat                                               20

<210> SEQ ID NO 29
<211> LENGTH: 24
<212> TYPE: DNA
<213> ORGANISM: Zea mays

<400> SEQUENCE: 29 tttttactc catctcatca catc                                           24

<210> SEQ ID NO 30
<211> LENGTH: 25
<212> TYPE: DNA
<213> ORGANISM: Zea mays

<400> SEQUENCE: 30
tgcttgtact gtagattatt tgagc                                         25

<210> SEQ ID NO 31
<211> LENGTH: 23
<212> TYPE: DNA
<213> ORGANISM: Zea mays

<400> SEQUENCE: 31
ttgttctcag ctaggccttg aat                                           23

<210> SEQ ID NO 32
<211> LENGTH: 20
<212> TYPE: DNA
<213> ORGANISM: Zea mays

<400> SEQUENCE: 32
gggactcgta gactggtgga                                               20

<210> SEQ ID NO 33
<211> LENGTH: 20
<212> TYPE: DNA
<213> ORGANISM: Zea mays

<400> SEQUENCE: 33
actgggatcg tcactttcgg                                               20

<210> SEQ ID NO 34
<211> LENGTH: 20
<212> TYPE: DNA
<213> ORGANISM: Zea mays

<400> SEQUENCE: 34

```
attccccccaa acagtggctt                                                    20

<210> SEQ ID NO 35
<211> LENGTH: 20
<212> TYPE: DNA
<213> ORGANISM: Zea mays

<400> SEQUENCE: 35
ggccccatga cgtgtagaga                                                     20

<210> SEQ ID NO 36
<211> LENGTH: 20
<212> TYPE: DNA
<213> ORGANISM: Zea mays

<400> SEQUENCE: 36
agtcccacac accatccaac                                                     20

<210> SEQ ID NO 37
<211> LENGTH: 20
<212> TYPE: DNA
<213> ORGANISM: Zea mays

<400> SEQUENCE: 37
ccctccaaaa cccaccacaa                                                     20

<210> SEQ ID NO 38
<211> LENGTH: 20
<212> TYPE: DNA
<213> ORGANISM: Zea mays

<400> SEQUENCE: 38
gtcccagtgg atgaccttgg                                                     20

<210> SEQ ID NO 39
<211> LENGTH: 20
<212> TYPE: DNA
<213> ORGANISM: Zea mays

<400> SEQUENCE: 39 cctttttgctt cagggttggg                                                    20

<210> SEQ ID NO 40
<211> LENGTH: 20
<212> TYPE: DNA
<213> ORGANISM: Zea mays

<400> SEQUENCE: 40
gtggcttcga cgagaagtga                                                     20

<210> SEQ ID NO 41
<211> LENGTH: 21
<212> TYPE: DNA
<213> ORGANISM: Zea mays

<400> SEQUENCE: 41
acacagccca tctcaggaaa g                                                   21

<210> SEQ ID NO 42
<211> LENGTH: 20
<212> TYPE: DNA
<213> ORGANISM: Zea mays

<400> SEQUENCE: 42
```

-continued

```
ggctggcttg ctcttaggaa                                               20

<210> SEQ ID NO 43
<211> LENGTH: 20
<212> TYPE: DNA
<213> ORGANISM: Zea mays

<400> SEQUENCE: 43
tcgtcgccca aatttcctga                                               20

<210> SEQ ID NO 44
<211> LENGTH: 20
<212> TYPE: DNA
<213> ORGANISM: Zea mays

<400> SEQUENCE: 44
cgaactgctt gggtctcagt                                               20
```

METHODS OF IDENTIFYING, SELECTING, AND PRODUCING SOUTHERN CORN RUST RESISTANT CROPS

CROSS-REFERENCE TO RELATED APPLICATIONS

This application is a national stage entry under 35 USC § 371 of PCT International Application Number PCT/US2019/032497, filed May 15, 2019, which claims priority to International Patent Application PCT/CN2018/090067 filed Jun. 6, 2018, the entire disclosures of which are incorporated herein by reference.

REFERENCE TO SEQUENCE LISTING SUBMITTED ELECTRONICALLY

A sequence listing having the file name "RTS22658_SeqList.txt" created on Apr. 30, 2019 and having a size of 91 kilobytes is filed in computer readable form concurrently with the specification. The sequence listing is part of the specification and is herein incorporated by reference in its entirety.

FIELD

The field is related to plant breeding and methods of identifying and selecting plants with resistance to southern corn rust. Provided are methods to identify novel genes that encode proteins providing plant resistance to southern corn rust and uses thereof. These disease resistant genes are useful in the production of resistant plants through breeding, transgenic modification, or genome editing.

BACKGROUND

Corn southern rust (SCR), a fungal disease caused by *Puccinia polysora* Underw, is a major disease in the tropical regions and southern part of the US and China. If SCR reaches the temperate regions (e.g. US Midwest) at critical points in the growing season and if conditions are favorable for rust development, disease intensity can reach epidemic levels very quickly, resulting in severe yield losses. Temperate maize germplasm is in general susceptible to SCR. The identification and utilization of resistance lines and QTL in breeding programs to develop varieties resistance to SCR represent a cost-effective way in controlling SCR. Alternatively, varieties carrying genes responsible to SCR resistance may be developed by transgenic or genome editing technologies. Identification of resistance QTL and genes would accelerate the development of products resistance to SCR. Resistance lines (e.g. Brewbaker, J. L., et al. "General resistance in maize to southern rust (*Puccinia polysora* Underw.)." Crop science 51, no. 4 (2011): 1393-1409) or QTL (e.g. Jines, M. P., et al. "Mapping resistance to Southern rust in a tropical by temperate maize recombinant inbred topcross population." Theoretical and Applied Genetics 114, no. 4 (2007): 659-667. Zhang, Y., et al. "Mapping of southern corn rust-resistant genes in the W2D inbred line of maize (*Zea mays* L.)." Molecular breeding 25, no. 3 (2010): 433-439. Zhou C J, et al. (2007) Characterization and fine mapping of RppQ, a resistance gene to southern corn rust in maize. Mol Genet Genomics 278:723-728. Holland, J. B., et al. "Inheritance of resistance to southern corn rust in tropical-by-corn-belt maize populations." Theoretical and Applied Genetics 96, no. 2 (1998): 232-241.) have been identified. However, none of the causal genes responsible for SCR resistance have been identified and characterized. There is a continuous need for disease-resistant plants and methods to find disease resistant genes.

SUMMARY

Compositions and methods useful in identifying and selecting plant disease resistance genes, or "R genes," are provided herein. The compositions and methods are useful in selecting disease resistant plants, creating transgenic resistant plants, and/or creating resistant genome edited plants. Plants having newly conferred or enhanced resistance various plant diseases as compared to control plants are also provided herein. In some embodiments, the compositions and methods are useful in selecting corn southern rust (SCR) disease resistant plants, creating transgenic SCR resistant plants, and/or creating SCR resistant genome edited plants.

An SCR resistant plant may be crossed to a second plant in order to obtain a progeny plant that has the resistant gene allele. The disease resistance may be newly conferred or enhanced relative to a control plant that does not have the favorable allele. The SCR R gene allele may be further refined to a chromosomal interval defined by and including defined markers. In some embodiments, the methods for identifying and/or selecting plants having resistance to SCR are presented. In these methods, DNA of a plant is analyzed for the presence of a resistant gene allele on chromosome 10 that is associated with SCR resistance, wherein said resistant gene allele comprises: an "A" at SNP001 (position 201 of reference sequence SEQ ID NO: 6), an "A" at SNP002 (position 127 of reference sequence SEQ ID NO: 7), a "C" at SNP003 (position 143 of reference sequence SEQ ID NO: 8), a "G" at S26 (position 43 of reference sequence SEQ ID NO: 1), an "A" at S27 (position 21 of reference sequence SEQ ID NO: 2), a "C" at S-24-1 (position 18 of reference sequence SEQ ID NO: 3), a "C" at S24-2 (position 19 of reference sequence SEQ ID NO: 3), a "G" at S24-3 (position 20 of reference sequence SEQ ID NO: 3), a "C" at S20-1 (position 17 of reference sequence SEQ ID NO: 4), a "T" at S20-2 (position 18 of reference sequence SEQ ID NO: 4), a "T" at S20-3 (position 21 of reference sequence SEQ ID NO: 4), a "C" at S28-1 (position 48 of reference sequence SEQ ID NO: 5), an "A" at S28-2 (position 49 of reference sequence SEQ ID NO: 5), a "T" at S28-3 (position 63 of reference sequence SEQ ID NO: 5), a "C" at S28-4 (position 64 of reference sequence SEQ ID NO: 5), an "A" at S28-5 (position 65 of reference sequence SEQ ID NO: 5), an "A" at S28-6 (position 66 of reference sequence SEQ ID NO: 5), a "G" at SNP004 (position 51 of reference sequence SEQ ID NO: 9), an "A" at SNP005 (position 39 of reference sequence SEQ ID NO: 10), and an "A" at SNP006 (position 23 of reference sequence SEQ ID NO: 11); and a plant is identified and/or selected as having SCR resistance if said resistant gene allele is detected. In some embodiments, the methods for identifying and/or selecting plants having resistance to SCR comprise detecting or selecting a genomic region comprising SEQ ID NO: 12. The SCR resistance may be newly conferred or enhanced relative to a control plant that does not have the favorable allele. In a further embodiment, the SCR resistant region comprises a gene encoding an RppK polypeptide that confers or enhances resistance to SCR (the "RppK gene"). In some embodiments, the RppK polypeptide comprises the amino acid sequence as set forth in SEQ ID NO: 14.

In another embodiment, methods of identifying and/or selecting plants with SCR resistance are provided in which one or more marker alleles linked to and associated with any of: an "A" at SNP001 (position 201 of reference sequence SEQ ID NO: 6), an "A" at SNP002 (position 127 of reference sequence SEQ ID NO: 7), a "C" at SNP003 (position 143 of reference sequence SEQ ID NO: 8), a "G" at S26 (position 43 of reference sequence SEQ ID NO: 1), an "A" at S27 (position 21 of reference sequence SEQ ID NO: 2), a "C" at S-24-1 (position 18 of reference sequence SEQ ID NO: 3), a "C" at S24-2 (position 19 of reference sequence SEQ ID NO: 3), a "G" at S24-3 (position 20 of reference sequence SEQ ID NO: 3), a "C" at S20-1 (position 17 of reference sequence SEQ ID NO: 4), a "T" at S20-2 (position 18 of reference sequence SEQ ID NO: 4), a "T" at S20-3 (position 21 of reference sequence SEQ ID NO: 4), a "C" at S28-1 (position 48 of reference sequence SEQ ID NO: 5), an "A" at S28-2 (position 49 of reference sequence SEQ ID NO: 5), a "T" at S28-3 (position 63 of reference sequence SEQ ID NO: 5), a "C" at S28-4 (position 64 of reference sequence SEQ ID NO: 5), an "A" at S28-5 (position 65 of reference sequence SEQ ID NO: 5), an "A" at S28-6 (position 66 of reference sequence SEQ ID NO: 5), a "G" at SNP004 (position 51 of reference sequence SEQ ID NO: 9), an "A" at SNP005 (position 39 of reference sequence SEQ ID NO: 10), and an "A" at SNP006 (position 23 of reference sequence SEQ ID NO: 11), are detected in a plant, and a plant having the one or more marker alleles is selected. The one or more marker alleles may be linked by 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, or 0.1 cM or less on a single meiosis based genetic map. The selected plant may be crossed to a second plant to obtain a progeny plant that has one or more marker alleles linked to and associated with any of: an "A" at SNP001 (position 201 of reference sequence SEQ ID NO: 6), an "A" at SNP002 (position 127 of reference sequence SEQ ID NO: 7), a "C" at SNP003 (position 143 of reference sequence SEQ ID NO: 8), a "G" at S26 (position 43 of reference sequence SEQ ID NO: 1), an "A" at S27 (position 21 of reference sequence SEQ ID NO: 2), a "C" at S-24-1 (position 18 of reference sequence SEQ ID NO: 3), a "C" at S24-2 (position 19 of reference sequence SEQ ID NO: 3), a "G" at S24-3 (position 20 of reference sequence SEQ ID NO: 3), a "C" at S20-1 (position 17 of reference sequence SEQ ID NO: 4), a "T" at S20-2 (position 18 of reference sequence SEQ ID NO: 4), a "T" at S20-3 (position 21 of reference sequence SEQ ID NO: 4), a "C" at S28-1 (position 48 of reference sequence SEQ ID NO: 5), an "A" at S28-2 (position 49 of reference sequence SEQ ID NO: 5), a "T" at S28-3 (position 63 of reference sequence SEQ ID NO: 5), a "C" at S28-4 (position 64 of reference sequence SEQ ID NO: 5), an "A" at S28-5 (position 65 of reference sequence SEQ ID NO: 5), an "A" at S28-6 (position 66 of reference sequence SEQ ID NO: 5), a "G" at SNP004 (position 51 of reference sequence SEQ ID NO: 9), an "A" at SNP005 (position 39 of reference sequence SEQ ID NO: 10), and an "A" at SNP006 (position 23 of reference sequence SEQ ID NO: 11).

In another embodiment, methods of introgressing a gene allele associated with SCR resistance are presented herein. In these methods, a population of plants is screened with one or more markers to determine if any of the plants has a gene allele associated with SCR resistance, and at least one plant that has the gene allele associated with SCR resistance is selected from the population. The gene allele comprises an "A" at SNP001 (position 201 of reference sequence SEQ ID NO: 6), an "A" at SNP002 (position 127 of reference sequence SEQ ID NO: 7), a "C" at SNP003 (position 143 of reference sequence SEQ ID NO: 8), a "G" at S26 (position 43 of reference sequence SEQ ID NO: 1), an "A" at S27 (position 21 of reference sequence SEQ ID NO: 2), a "C" at S-24-1 (position 18 of reference sequence SEQ ID NO: 3), a "C" at S24-2 (position 19 of reference sequence SEQ ID NO: 3), a "G" at S24-3 (position 20 of reference sequence SEQ ID NO: 3), a "C" at S20-1 (position 17 of reference sequence SEQ ID NO: 4), a "T" at S20-2 (position 18 of reference sequence SEQ ID NO: 4), a "T" at S20-3 (position 21 of reference sequence SEQ ID NO: 4), a "C" at S28-1 (position 48 of reference sequence SEQ ID NO: 5), an "A" at S28-2 (position 49 of reference sequence SEQ ID NO: 5), a "T" at S28-3 (position 63 of reference sequence SEQ ID NO: 5), a "C" at S28-4 (position 64 of reference sequence SEQ ID NO: 5), an "A" at S28-5 (position 65 of reference sequence SEQ ID NO: 5), an "A" at S28-6 (position 66 of reference sequence SEQ ID NO: 5), a "G" at SNP004 (position 51 of reference sequence SEQ ID NO: 9), an "A" at SNP005 (position 39 of reference sequence SEQ ID NO: 10), and an "A" at SNP006 (position 23 of reference sequence SEQ ID NO: 11).

In some embodiments, introgression of SCR resistant genes from resistant to susceptible lines may be achieved either by marker-assisted trait introgression, transgenic, or genome editing approaches.

Embodiments include an isolated polynucleotide comprising a nucleotide sequence encoding a RppK polypeptide capable of conferring resistance to SCR, wherein the RppK polypeptide has an amino acid sequence of at least 50%, at least 75%, at least 80%, at least 85%, at least 90%, at least 95% identity, at least 96% identity, at least 97% identity, at least 98% identity, or at least 99% identity when compared to SEQ ID NO: 14. In another embodiment, an isolated polynucleotide comprises a nucleotide sequence encoding a RppK polypeptide capable of conferring resistance to SCR, wherein the RppK polypeptide has an amino acid sequence of at least 50%, at least 75%, at least 80%, at least 85%, at least 90%, and at least 95% identity, when compared to SEQ ID NO: 14.

Additional embodiments of the present disclosure include a vector comprising a polynucleotide of the disclosure, such as SEQ ID NO: 13, or a recombinant DNA construct comprising a polynucleotide disclosed herein operably linked to at least one regulatory sequence. A plant cell, as well as a plant, each comprising the recombinant DNA construct of an embodiment disclosed herein, and a seed comprising the recombinant DNA construct are also embodied.

In some embodiments, the compositions and methods relate to a modified plant having increased resistance to a disease, wherein the allele causing the increased disease resistance comprises a nucleotide sequence encoding a RppK resistance gene, wherein the RppK resistance gene is at least 50%, at least 75%, at least 80%, at least 85%, at least 90%, and at least 95% identity, at least 96% identity, at least 97% identity, at least 98% identity, or at least 99% identity to the sequence set forth in SEQ ID NO: 13.

The methods embodied by the present disclosure relate to a method for transforming a host cell, including a plant cell, comprising transforming the host cell with the polynucleotide of an embodiment of the present disclosure; a method for producing a plant comprising transforming a plant cell with the recombinant DNA construct of an embodiment of the present disclosure and regenerating a plant from the transformed plant cell, and methods of conferring or enhancing disease resistance, comprising transforming a plant with the recombinant DNA construct disclosed herein.

Methods of altering the level of expression of a protein capable of conferring disease resistance in a plant or plant cell comprising (a) transforming a plant cell with a recombinant DNA construct disclosed herein and (b) growing the transformed plant cell under conditions that are suitable for expression of the recombinant DNA construct wherein expression of the recombinant DNA construct results in production of altered levels of a protein capable of conferring disease resistance in the transformed host are also embodied.

Plants identified and/or selected using any of the methods presented above are also provided.

DESCRIPTION OF THE DRAWINGS

FIG. 1 shows a linkage analysis of RppK. Numbers between two markers indicate the genetic distance (upper) or number of recombinants (middle) of each interval. Recombination breakpoints of key recombinants and annotated genes within the final RppK interval are shown.

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The NBS-LRR ("NLR") group of R-genes is the largest class of R-genes discovered to date. In *Arabidopsis thaliana*, over 150 are predicted to be present in the genome (Meyers, et al., (2003), Plant Cell, 15:809-834; Monosi, et al., (2004), Theoretical and Applied Genetics, 109:1434-1447), while in rice, approximately 500 NLR genes have been predicted (Monosi, (2004) supra). The NBS-LRR class of R genes is comprised of two subclasses. Class 1 NLR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) Genome Research, 12:1871-1884; Monosi, (2004) supra; Pan, et al., (2000), Journal of Molecular Evolution, 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), Current Biology: CB, 8:R226-R227). The LRR region appears to be the region that interacts with the pathogen AVR products (Michelmore, et al., (1998), Genome Res., 8:1113-1130; Meyers, (2003) supra). This LRR region in comparison with the NB-ARC (NBS) domain is under a much greater selection pressure to diversify (Michelmore, (1998) supra; Meyers, (2003) supra; Palomino, et al., (2002), Genome Research, 12:1305-1315). LRR domains are found in other contexts as well; these 20-29-residue motifs are present in tandem arrays in a number of proteins with diverse functions, such as hormone-receptor interactions, enzyme inhibition, cell adhesion and cellular trafficking. A number of recent studies revealed the involvement of LRR proteins in early mammalian development, neural development, cell polarization, regulation of gene expression and apoptosis signaling.

An allele is "associated with" a trait when it is part of or linked to a DNA sequence or allele that affects the expression of the trait. The presence of the allele is an indicator of how the trait will be expressed.

As used to herein, "disease resistant" or "have resistance to a disease" refers to a plant showing increase resistance to a disease compared to a control plant. Disease resistance may manifest in fewer and/or smaller lesions, increased plant health, increased yield, increased root mass, increased plant vigor, less or no discoloration, increased growth, reduced necrotic area, or reduced wilting. In some embodiments, an allele may show resistance one or more diseases.

Disease affecting maize plants include, but are not limited to, bacterial leaf blight and stalk rot; bacterial leaf spot; bacterial stripe; chocolate spot; goss's bacterial wilt and blight; holcus spot; purple leaf sheath; seed rot-seedling blight; bacterial wilt; corn stunt; anthracnose leaf blight; anthracnose stalk rot; *Aspergillus* ear and kernel rot; banded leaf and sheath spot; black bundle disease; black kernel rot; borde blanco; brown spot; black spot; stalk rot; *Cephalosporium* kernel rot; charcoal rot; corticium ear rot; curvularia leaf spot; didymella leaf spot; *Diplodia* ear rot and stalk rot; *Diplodia* ear rot; seed rot; corn seedling blight; *Diplodia* leaf spot or leaf streak; downy mildews; brown stripe downy mildew; crazy top downy mildew; green ear downy mildew; *Graminicola* downy mildew; java downy mildew; philippine downy mildew; sorghum downy mildew; *Spontaneum* downy mildew; sugarcane downy mildew; dry ear rot; ergot; horse's tooth; corn eyespot; *Fusarium* ear and stalk rot; *Fusarium* blight; seedling root rot; *Gibberella* ear and stalk rot; gray ear rot; gray leaf spot; *Cercospora* leaf spot; *Helminthosporium* root rot; hormodendrum ear rot; *Cladosporium* rot; hyalothyridium leaf spot; late wilt; northern leaf blight; white blast; crown stalk rot; corn stripe; northern leaf spot; *Helminthosporium* ear rot; *Penicillium* ear rot; corn blue eye; blue mold; phaeocytostroma stalk rot and root rot; phaeosphaeria leaf spot; *Physalospora* ear rot; *Botryosphaeria* ear rot; *Pyrenochaeta* stalk rot and root rot; *Pythium* root rot; *Pythium* stalk rot; red kernel disease; *Rhizoctonia* ear rot; sclerotial rot; *Rhizoctonia* root rot and stalk rot; *Rostratum* leaf spot; common corn rust; southern corn rust; tropical corn rust; *Sclerotium* ear rot; southern blight; selenophoma leaf spot; sheath rot; shuck rot; silage mold; common smut; false smut; head smut; southern corn leaf blight and stalk rot; southern leaf spot; tar spot; *Trichoderma* ear rot and root rot; white ear rot, root and stalk rot; yellow leaf blight; zonate leaf spot; american wheat striate (wheat striate mosaic); barley stripe mosaic; barley yellow dwarf; brome mosaic; cereal chlorotic mottle; lethal necrosis (maize lethal necrosis disease); cucumber mosaic; johnsongrass mosaic; maize bushy stunt; maize chlorotic dwarf; maize chlorotic mottle; maize dwarf mosaic; maize leaf fleck; maize pellucid ringspot; maize rayado fino; maize red leaf and red stripe; maize red stripe; maize ring mottle; maize rough dwarf; maize sterile stunt; maize streak; maize stripe; maize tassel abortion; maize vein enation; maize wallaby ear; maize white leaf; maize white line mosaic; millet red leaf; and northern cereal mosaic.

Disease affecting plants include, but are not limited to, bacterial blight; bacterial leaf streak; foot rot; grain rot; sheath brown rot; blast; brown spot; crown sheath rot; downy mildew; eyespot; false smut; kernel smut; leaf smut; leaf scald; narrow brown leaf spot; root rot; seedling blight; sheath blight; sheath rot; sheath spot; *Alternaria* leaf spot; and stem rot.

Disease affecting soybean plants include, but are not limited to, *Alternaria* leaf spot; anthracnose; black leaf blight; black root rot; brown spot; brown stem rot; charcoal rot; *Choanephora* leaf blight; downy mildew; *Drechslera* blight; frogeye leaf spot; *Leptosphaerulina* leaf spot; *Mycoleptodiscus* root rot; *Neocosmospora* stem rot; *Phomopsis* seed decay; *Phytophthora* root and stem rot; *Phyllosticta* leaf spot; *Phymatotrichum* root rot; pod and stem blight; powdery mildew; purple seed stain; *Pyrenochaeta* leaf spot; *Pythium* rot; red crown rot; *Dactuliophora* leaf spot; *Rhizoctonia* aerial blight; *Rhizoctonia* root and stem rot; rust; scab; *Sclerotinia* stem rot; *Sclerotium* blight; stem canker; *Stemphylium* leaf blight; sudden death syndrome; target spot; yeast spot; lance nematode; lesion nematode; pin nematode; reniform nematode; ring nematode; root-knot nematode; sheath nematode; cyst nematode; spiral nematode; sting nematode; stubby root nematode; stunt nematode; alfalfa mosaic; bean pod mottle; bean yellow mosaic; brazilian bud blight; chlorotic mottle; yellow mosaic; peanut mottle; peanut stripe; peanut stunt; chlorotic mottle; crinkle leaf; dwarf; severe stunt; and tobacco ringspot or bud blight.

Disease affecting canola plants include, but are not limited to, bacterial black rot; bacterial leaf spot; bacterial pod rot; bacterial soft rot; scab; crown gall; *Alternaria* black spot; anthracnose; black leg; black mold rot; black root; brown girdling root rot; *Cercospora* leaf spot; clubroot; downy mildew; *Fusarium* wilt; gray mold; head rot; leaf spot; light leaf spot; pod rot; powdery mildew; ring spot; root rot; *Sclerotinia* stem rot; seed rot, damping-off; root gall smut; southern blight; *Verticillium* wilt; white blight; white leaf spot; staghead; yellows; crinkle virus; mosaic virus; yellows virus;

Disease affecting sunflower plants include, but are not limited to, apical chlorosis; bacterial leaf spot; bacterial wilt; crown gall; *Erwinia* stalk rot and head rot; lternaria leaf blight, stem spot and head rot; *Botrytis* head rot; charcoal rot; downy mildew; *Fusarium* stalk rot; *Fusarium* wilt; *Myrothecium* leaf and stem spot; *Phialophora* yellows; *Phoma* black stem; *Phomopsis* brown stem canker; *Phymatotrichum* root rot; *Phytophthora* stem rot; powdery mildew; *Pythium* seedling blight and root rot; *Rhizoctonia* seedling blight; *Rhizopus* head rot; sunflower rust; *Sclerotium* basal stalk and root rot; *Septoria* leaf spot; *Verticillium* wilt; white rust; yellow rust; dagger; pin; lesion; reniform; root knot; and chlorotic mottle;

Disease affecting sorghum plants include, but are not limited to, bacterial leaf spot; bacterial leaf streak; bacterial leaf stripe; *Acremonium* wilt; anthracnose; charcoal rot; crazy top downy mildew; damping-off and seed rot; ergot; *Fusarium* head blight, root and stalk rot; grain storage mold; gray leaf spot; latter leaf spot; leaf blight; milo disease; oval leaf spot; pokkah boeng; *Pythium* root rot; rough leaf spot; rust; seedling blight and seed rot; smut, covered kernel; smut, head; smut, loose kernel; sooty stripe; downy mildew; tar spot; target leaf spot; and zonate leaf spot and sheath blight.

A plant having disease resistance may have 5, 10, 15, 20, 25, 30, 35, 40, 45, 50, 55, 60, 65, 70, 75, 80, 85, 90, 95, or 100% increased resistance to a disease compared to a control plant. In some embodiments, a plant may have 5, 10, 15, 20, 25, 30, 35, 40, 45, 50, 55, 60, 65, 70, 75, 80, 85, 90, 95, or 100% increased plant health in the presence of a disease compared to a control plant.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to southern corn rust). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

An "elite line" is any line that has resulted from breeding and selection for superior agronomic performance.

An "exotic strain," a "tropical line," or an "exotic germplasm" is a strain derived from a plant not belonging to an available elite line or strain of germplasm. In the context of a cross between two plants or strains of germplasm, an exotic germplasm is not closely related by descent to the elite germplasm with which it is crossed. Most commonly, the exotic germplasm is not derived from any known elite line, but rather is selected to introduce novel genetic elements (typically novel alleles) into a breeding program.

A "favorable allele" is the allele at a particular locus (a marker, a QTL, a gene etc.) that confers, or contributes to, an agronomically desirable phenotype, e.g., disease resistance, and that allows the identification of plants with that agronomically desirable phenotype. A favorable allele of a marker is a marker allele that segregates with the favorable phenotype.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Learning Corn.

The term "homogeneity" indicates that members of a group have the same genotype at one or more specific loci.

The term "hybrid" refers to the progeny obtained between the crossing of at least two genetically dissimilar parents.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meiosis). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

The term "plant" includes whole plants, plant cells, plant protoplast, plant cell or tissue culture from which plants can be regenerated, plant calli, plant clumps and plant cells that are intact in plants or parts of plants, such as seeds, flowers, cotyledons, leaves, stems, buds, roots, root tips and the like. As used herein, a "modified plant" means any plant that has a genetic change due to human intervention. A modified plant may have genetic changes introduced through plant transformation, genome editing, or conventional plant breeding A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

A "production marker" or "production SNP marker" is a marker that has been developed for high-throughput purposes. Production SNP markers are developed to detect specific polymorphisms and are designed for use with a variety of chemistries and platforms.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Marker loci that demonstrate statistically significant co-segregation with a disease resistance trait that confers broad resistance against a specified disease or diseases are provided herein. Detection of these loci or additional linked loci and the resistance gene may be used in marker assisted selection as part of a breeding program to produce plants that have resistance to a disease or diseases.

Genetic Mapping

It has been recognized for quite some time that specific genetic loci correlating with particular phenotypes, such as disease resistance, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as a disease resistance trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis (i.e. association mapping) and 2) Traditional linkage analysis.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," *Nat Genet* 7:180-184; Hastbacka et al. (1992) "Linkage disequilibrium mapping in isolated founder populations: diastrophic dysplasia in Finland," *Nat Genet* 2:204-211; Kerem et al. (1989) "Identification of the cystic fibrosis gene: genetic analysis," *Science* 245:1073-1080) and maize (Remington et al., (2001) "Structure of linkage disequilibrium and phenotype associations in the maize genome," *Proc Natl Acad Sci USA* 98:11479-11484; Thornsberry et al. (2001) "Dwarf8 polymorphisms associate with variation in flowering time," *Nat Genet* 28:286-289; reviewed by Flint-Garcia et al. (2003) "Structure of linkage disequilibrium in plants," *Annu Rev Plant Biol.* 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," *Nat Rev Genet* 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants," *Annu Rev Plant Biol.* 54:357-374).

Elite breeding lines provide a valuable starting point for association analyses. Association analyses use quantitative phenotypic scores (e.g., disease tolerance rated from one to nine for each line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable map (for example, a composite map) can optionally be used to help observe distribution of the identified QTL markers and/or QTL marker clustering using previously determined map locations of the markers.

Traditional Linkage Analysis

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Marker loci that demonstrate statistically significant co-segregation with a disease resistance trait, as determined by traditional linkage analysis and by whole genome association analysis, are provided herein. Detection of these loci or additional linked loci can be used in marker assisted breeding programs to produce plants having disease resistance.

Activities in marker assisted breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

Chromosomal Intervals

Chromosomal intervals that correlate with the disease resistance trait are provided. A variety of methods well known in the art are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for a disease resistance trait.

Conversely, e.g., if two markers in close proximity show co-segregation with the desired phenotypic trait, it is sometimes unclear if each of those markers identify the same gene or two different gene or multiple genes. Regardless, knowledge of how many genes are in a particular physical/genomic interval is not necessary to make or practice that which is presented in the current disclosure.

The chromosome 10 interval may encompass any of the markers identified herein as being associated with the SCR resistance trait including an "A" at SNP001 (position 201 of reference sequence SEQ ID NO: 6), an "A" at SNP002 (position 127 of reference sequence SEQ ID NO: 7), a "C" at SNP003 (position 143 of reference sequence SEQ ID NO: 8), a "G" at S26 (position 43 of reference sequence SEQ ID NO: 1), an "A" at S27 (position 21 of reference sequence SEQ ID NO: 2), a "C" at S-24-1 (position 18 of reference sequence SEQ ID NO: 3), a "C" at S24-2 (position 19 of reference sequence SEQ ID NO: 3), a "G" at S24-3 (position 20 of reference sequence SEQ ID NO: 3), a "C" at S20-1 (position 17 of reference sequence SEQ ID NO: 4), a "T" at S20-2 (position 18 of reference sequence SEQ ID NO: 4), a "T" at S20-3 (position 21 of reference sequence SEQ ID NO: 4), a "C" at S28-1 (position 48 of reference sequence SEQ ID NO: 5), an "A" at S28-2 (position 49 of reference sequence SEQ ID NO: 5), a "T" at S28-3 (position 63 of reference sequence SEQ ID NO: 5), a "C" at S28-4 (position 64 of reference sequence SEQ ID NO: 5), an "A" at S28-5 (position 65 of reference sequence SEQ ID NO: 5), an "A" at S28-6 (position 66 of reference sequence SEQ ID NO: 5), a "G" at SNP004 (position 51 of reference sequence SEQ ID NO: 9), an "A" at SNP005 (position 39 of reference sequence SEQ ID NO: 10), and an "A" at SNP006 (position 23 of reference sequence SEQ ID NO: 11). Any marker located within these intervals can find use as a marker for SCR resistance and can be used in the context of the methods presented herein to identify and/or select plants that have resistance to SCR, whether it is newly conferred or enhanced compared to a control plant. In certain embodiments, markers located upstream and downstream of RppK gene position are very tightly linked genetically and physically and hence may be used to select the RppK gene for trait introgression and products development.

Chromosomal intervals can also be defined by markers that are linked to (show linkage disequilibrium with) a disease resistant gene, and $r^2$ is a common measure of linkage disequilibrium (LD) in the context of association studies. If the $r^2$ value of LD between a chromosome 7 marker locus in an interval of interest and another chromosome 7 marker locus in close proximity is greater than 1/3 (Ardlie et al., Nature Reviews Genetics 3:299-309 (2002)), the loci are in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with the disease resistance trait, it is important to note that the marker locus is not necessarily responsible for the expression of the disease resistance phenotype. For example, it is not a requirement that the marker polynucleotide sequence be part of a gene that is responsible for the disease resistant phenotype (for example, is part of the gene open reading frame). The association between a specific marker allele and the disease resistance trait is due to the original "coupling" linkage phase between the marker allele and the allele in the ancestral line from which the allele originated. Eventually, with repeated recombination, crossing over events between the marker and genetic locus can change this orientation. For this reason, the favorable marker allele may change depending on the linkage phase that exists within the parent having resistance to the disease that is used to create segregating populations. This does not change the fact that the marker can be used to monitor segregation of the phenotype. It only changes which marker allele is considered favorable in a given segregating population.

Methods presented herein include detecting the presence of one or more marker alleles associated with disease resistance in a plant and then identifying and/or selecting plants that have favorable alleles at those marker loci. Markers have been identified herein as being associated with the disease resistance trait and hence can be used to predict disease resistance in a plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM (based on a single meiosis based genetic map) could also be used to predict disease resistance in a plant.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. In some embodiments, the methods disclosed herein produce a marker in a disease resistance gene, wherein the gene was identified by inferring genomic location from clustering of conserved domains or a clustering analysis.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as SNPs do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing, and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele "T" for a specific line or variety with disease resistance, but the allele 'T' might also occur in the breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the markers presented herein can readily be used as single nucleotide polymorphic (SNP) markers to select for the RppK gene. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically, with respect to the fine map information described herein, one can readily use the information provided herein to obtain additional polymorphic SNPs (and other markers) within the region amplified by the primers disclosed herein. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the species, or even across other species that have been genetically or physically aligned.

In general, MAS uses polymorphic markers that have been identified as having a significant likelihood of co-segregation with a trait such as the SCR disease resistance trait. Such markers are presumed to map near a gene or genes that give the plant its disease resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with SCRdisease resistance may be selected for by detecting one or more marker alleles, and in addition, progeny plants derived from those plants can also be selected. Hence, a plant containing a desired genotype in a given chromosomal region (i.e. a genotype associated with disease resistance) is obtained and then crossed to another plant. The progeny of such a cross would then be evaluated genotypically using one or more markers and the progeny plants with the same genotype in a given chromosomal region would then be selected as having disease resistance.

The SNPs could be used alone or in combination (i.e. a SNP haplotype) to select for a favorable resistant gene allele associated with SCR disease resistance. For example, a SNP haplotype at the chromosome 10 QTL disclosed herein can comprise: an "A" at SNP001 (position 201 of reference sequence SEQ ID NO: 6), an "A" at SNP002 (position 127 of reference sequence SEQ ID NO: 7), a "C" at SNP003 (position 143 of reference sequence SEQ ID NO: 8), a "G" at S26 (position 43 of reference sequence SEQ ID NO: 1), an "A" at S27 (position 21 of reference sequence SEQ ID NO: 2), a "C" at S-24-1 (position 18 of reference sequence SEQ ID NO: 3), a "C" at S24-2 (position 19 of reference sequence SEQ ID NO: 3), a "G" at S24-3 (position 20 of reference sequence SEQ ID NO: 3), a "C" at S20-1 (position 17 of reference sequence SEQ ID NO: 4), a "T" at S20-2 (position 18 of reference sequence SEQ ID NO: 4), a "T" at S20-3 (position 21 of reference sequence SEQ ID NO: 4), a "C" at S28-1 (position 48 of reference sequence SEQ ID NO: 5), an "A" at S28-2 (position 49 of reference sequence SEQ ID NO: 5), a "T" at S28-3 (position 63 of reference sequence SEQ ID NO: 5), a "C" at S28-4 (position 64 of reference sequence SEQ ID NO: 5), an "A" at S28-5 (position 65 of reference sequence SEQ ID NO: 5), an "A" at S28-6 (position 66 of reference sequence SEQ ID NO: 5), a "G" at SNP004 (position 51 of reference sequence SEQ ID NO: 9), an "A" at SNP005 (position 39 of reference sequence SEQ ID NO: 10), and an "A" at SNP006 (position 23 of reference sequence SEQ ID NO: 11), or a combination thereof.

The skilled artisan would expect that there might be additional polymorphic sites at marker loci in and around a chromosome marker identified by the methods disclosed herein, wherein one or more polymorphic sites is in linkage disequilibrium (LD) with an allele at one or more of the polymorphic sites in the haplotype and thus could be used in a marker assisted selection program to introgress a gene allele or genomic fragment of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the disease resistance trait QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

Plants identified, modified, and/or selected by any of the methods described above are also of interest.

Proteins and Variants and Fragments Thereof

RppK polypeptides are encompassed by the disclosure. "RppK polypeptide" and "RppK protein" as used herein interchangeably refers to a polypeptide(s) having SCR resistance activity, and is sufficiently identical to the RppK polypeptide of SEQ ID NO: 14. A variety of RppK polypeptides are contemplated.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In some embodiments the sequence identity is against the full length sequence of a polypeptide. The term "about" when used herein in context with percent sequence identity means+/−1.0%.

A "recombinant protein" is used herein to refer to a protein that is no longer in its natural environment, for example in vitro or in a recombinant bacterial or plant host cell; a protein that is expressed from a polynucleotide that has been edited from its native version; or a protein that is expressed from a polynucleotide in a different genomic position relative to the native sequence.

"Substantially free of cellular material" as used herein refers to a polypeptide including preparations of protein having less than about 30%, 20%, 10% or 5% (by dry weight) of non-target protein (also referred to herein as a "contaminating protein").

"Fragments" or "biologically active portions" include polypeptide or polynucleotide fragments comprising sequences sufficiently identical to an RppK polypeptide or polynucleotide, respectively, and that exhibit disease resistance when expressed in a plant.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments a RppK polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the full length or a fragment of the amino acid sequence of SEQ ID NO: 14, wherein the RppK polypeptide has SCR resistance when expressed in a plant.

Methods for such manipulations are generally known in the art. For example, amino acid sequence variants of an RppK polypeptide may be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired activity. However, it is understood that the ability of an RppK polypeptide to confer disease resistance may be improved by the use of such techniques upon the compositions of this disclosure.

Nucleic Acid Molecules and Variants and Fragments Thereof

Isolated or recombinant nucleic acid molecules comprising nucleic acid sequences encoding RppK polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell; has been edited from its native sequence; or is located in a different location than the native sequence. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding RppK polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding RppK polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an RppK polypeptide is a non-genomic sequence.

A variety of polynucleotides that encode RppK polypeptides or related proteins are contemplated. Such polynucleotides are useful for production of RppK polypeptides in host cells when operably linked to a suitable promoter, transcription termination and/or polyadenylation sequences. Such polynucleotides are also useful as probes for isolating homologous or substantially homologous polynucleotides that encode RppK polypeptides or related proteins.

In some embodiments the nucleic acid molecule encoding an RppK polypeptide is a polynucleotide having the sequence set forth in SEQ ID NO: 13, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the RppK polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an RppK polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 13, wherein the RppK polypeptide has SCR resistance activity when expressed in a plant.

In some embodiments the nucleic acid molecule encodes an RppK polypeptide variant comprising one or more amino acid substitutions to the amino acid sequence of SEQ ID NO: 14.

Nucleic acid molecules that are fragments of these nucleic acid sequences encoding RppK polypeptides are also encompassed by the embodiments. "Fragment" as used herein refers to a portion of the nucleic acid sequence encoding an RppK polypeptide. A fragment of a nucleic acid sequence may encode a biologically active portion of an RppK polypeptide or it may be a fragment that can be used as a hybridization probe or PCR primer using methods disclosed below. Nucleic acid molecules that are fragments of a nucleic acid sequence encoding an RppK polypeptide comprise at least about 150, 180, 210, 240, 270, 300, 330, 360, 400, 450, or 500 contiguous nucleotides or up to the number of nucleotides present in a full-length nucleic acid sequence encoding a RppK polypeptide identified by the methods disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the RppK polypeptide and, hence, retain disease resistance. "Retains disease resistance" is used herein to refer to a polypeptide having at least about 10%, at least about 30%, at least about 50%, at least about 70%, 80%, 90%, 95% or higher of the disease resistance of the full-length RppK polypeptide as set forth in SEQ ID NO: 14.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments a RppK polynucleotide encodes a RppK polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 14.

The embodiments also encompass nucleic acid molecules encoding RppK polypeptide variants. "Variants" of RppK polypeptide encoding nucleic acid sequences include those sequences that encode the RppK polypeptides identified by the methods disclosed herein, but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the RppK polypeptides disclosed herein.

The skilled artisan will further appreciate that changes can be introduced by mutation of the nucleic acid sequences thereby leading to changes in the amino acid sequence of the encoded RppK polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. such activity at a desired pH, etc. This can include identifying any activity that can be detected, for example, in an automated or automatable format, by any of the assays in the art. A variety of related (or even unrelated) properties can be evaluated, in serial or in parallel, at the discretion of the practitioner.

The nucleotide sequences of the embodiments can also be used to isolate corresponding sequences from a different source. In this manner, methods such as PCR, hybridization, and the like can be used to identify such sequences based on their sequence homology to the sequences identified by the methods disclosed herein. Sequences that are selected based on their sequence identity to the entire sequences set forth herein or to fragments thereof are encompassed by the embodiments. Such sequences include sequences that are orthologs of the sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (*Academic Press*, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization methods, all or part of the nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding polypeptides or a fragment or variant thereof. Methods for the preparation of probes for hybridization and stringency conditions are generally known in the art and are disclosed in Sambrook and Russell, (2001), supra.

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an RppK polypeptide of the embodiments. In some embodiments the DNA construct comprises a polynucleotide encoding a fusion protein comprising an RppK polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91: 151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the plant-preferred for a particular amino acid may be derived from known gene sequences from plants.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

Methods to Introduce Genome Editing Technologies into Plants

In some embodiments, polynucleotide compositions can be introduced into the genome of a plant using genome editing technologies, or previously introduced polynucleotides in the genome of a plant may be edited using genome editing technologies. For example, the identified polynucleotides can be introduced into a desired location in the genome of a plant through the use of double-stranded break technologies such as TALENs, meganucleases, zinc finger nucleases, CRISPR-Cas, and the like. For example, the identified polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where an SCR resistance RppK gene allele has been identified in a genome, genome editing technologies may be used to alter or modify the polynucleotide sequence. Site specific modifications that can be introduced into the desired RppK gene allele polynucleotide include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional disease resistant proteins in close proximity to the RppK polynucleotide compositions within the genome of a plant, in order to generate molecular stacks disease resistant proteins.

An "altered target site," "altered target sequence," "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

EXAMPLES

The following examples are offered to illustrate, but not to limit, the claimed subject matter. It is understood that the examples and embodiments described herein are for illustrative purposes only, and persons skilled in the art will recognize various reagents or parameters that can be altered without departing from the spirit of the disclosure or the scope of the appended claims.

Example 1. Identification of a Major Resistance QTL to SCR from K22 and Fine Mapping of RppK Southern corn rust (SCR), caused by the biotrophic pathogen *Puccinia polysora*, is a major disease in many maize-growing regions. High temperature and humidity conditions usually favor the development of SCR. The severity of SCR in field experiments is rated by visual inspection 3-4 weeks after pollination, using the nine-point scale, with 1 being the most resistant and 9 being the most susceptible. Ratings "1" indicates no disease symptoms on leaf. Ratings "2" means 0-5 percent of leaf area pustules infected. Rating "3" means 5-25 percent of leaf area infected. Rating "4" means the 25-40 percent of leaf area infected. Rating "5" means the 40-50 percent of leaf area pustules infected. Rating "6" means the 50-60 percent of leaf area pustules infected. Rating "7" means the 60-75 percent of leaf area pustules infected. Rating "8" means the 75-90 percent of leaf area pustules infected. Rating "9" means the whole leaf was infected pustules and dying. Inbred line K22 has been identified as a strong resistant line to SCR, consistently scored as "1".

Maize inbred line K22, a resistant line to SCR, was crossed to two SCR susceptible lines, Dan340 and By815, and two recombinant inbred line (RIL) populations were developed by self-pollinating for six generations using the single seed descent method. The K22×Dan340 and K22×By815 populations consist of 192 and 207 RILs, respectively. The two populations were genotyped with the Illumina MaizeSNP50K chip and scored for SCR resistance in multiple year×location experiments. A major QTL (RppK) on chromosome 10 was identified in both populations (Table 1), and the QTL interval is flanked by SNP markers SYN16185 and SYN16808. Additional flanking markers, RRD39 and RRD40 from one side and RRD26 and SSR4 on the other side of RppK, were identified through linkage mapping. Primer information for the markers used in RppK mapping is listed in Table 2.

TABLE 1

The QTLs detected in two RILs (K22/Dan340 and K22/BY815) by CIM method

| Population | Chr. | Left marker | Position of left markers (B73 V2) | Right marker | Position of right markers (B73 V2) |
|---|---|---|---|---|---|
| K22/DAN340 | 8 | PZE-108092412 | 149.4 Mb | PZE-108092671 | 149.8 Mb |
|  | 10 | SYN16185 | 2.04 Mb | SYN16808 | 2.26 Mb |
| K22/BY815 | 2 | PZE-102128040 | — | PZE-102130759 | 178.0 Mb |
|  | 3 | SYN6785 | 216.3 Mb | SYN28000 | 217.3 Mb |
|  | 7 | PZE-107067197 | 118.5 Mb | SYN19272 | 120.8 Mb |
|  | 10 | PZE-110001138 | 1.95 Mb | PZE-110002524 | 2.47 Mb |

TABLE 2

Primers for Markers for QTL Mapping

| Primer name | Forward primer (5'-3') | Reverse primer (5'-3') | Type | SEQ ID NOs:* |
|---|---|---|---|---|
| RRD39 | GGAAAGCCTGAGTGCTGGAA | CCGCTGACTTGGCTGTAAGT | SSR | 15 and 16 |
| RRD40 | AGTTCAGGGCAGTTCACCAC | TAACGGCTTGGCCCAACTAC | SSR | 17 and 18 |
| InDel7-3 | GTTCATTCGTTTCTAATACAGTGGC | TATCAGCGGATACGTACAGCACC | InDel | 19 and 20 |
| RRD103 | GGCTGGTTGCGCTAAAATAG | TTTTTCGCTTGCATTTGTTG | SSR | 21 and 22 |
| RRD111 | TCATCATCCCATATGTCATCAAC | GGCAGTTTTGCCATGTTTATATG | SSR | 23 and 24 |
| InDel213 | AGGAGCCAAGATCCTACCGT | CATTTAGGGCCGGTGAGACA | InDel | 25 and 26 |
| SSR258-3 | AGATGGCGATAGCTGCATGG | GCGCCCACGGTATACATCAT | SSR | 27 and 28 |
| InDel262-2 | TTTTTTACTCCATCTCATCACATC | TGCTTGTACTGTAGATTATTTGAGC | InDel | 29 and 30 |
| RRD64 | TTGTTCTCAGCTAGGCCTTGAAT | GGGACTCGTAGACTGGTGGA | SSR | 31 and 32 |
| RRD26 | ACTGGGATCGTCACTTTCGG | ATTCCCCCAAACAGTGGCTT | SSR | 33 and 34 |
| SSR4 | GGCCCCATGACGTGTAGAGA | AGTCCCACACACCATCCAAC | SSR | 35 and 36 |
| RRD15 | CCCTCCAAAACCCACCACAA | GTCCCAGTGGATGACCTTGG | SSR | 37 and 38 |

*Forward primer listed first, reverse primer listed second.

Nine RILs from the K22×Dan340 population and with residual heterozygosity at the RppK locus (heterogeneous inbred families or HIFs) were self-pollinated to generate a large segregating population (HIF-F2). A total of 3392 HIF-H2 individuals were genotyped with two flanking markers, RRD39 and SSR4, and 402 recombinants were identified. The recombinants and their progenies were evaluated for SCR resistance, and additional markers were developed within the interval to genotype the recombinants. Finally, RppK was delimited to an interval between markers SNP20 and SNP5, and marker RRD77 co-segregates perfectly with RppK (See Table 3 for K22 resistant allele haplotype SNPs).

TABLE 3

K22 Resistant Allele Haplotype SNPs

| Description | Chromosome | Position (B73v4) | K22 Resistant | DAN340 Susceptible | B73 Susceptible | Reference SEQ ID NO: |
|---|---|---|---|---|---|---|
| SNP001 | 10 | 1566820 | A | Unknown | G | 6 |
| SNP002 | 10 | 1570886 | A | Unknown | G | 7 |
| SNP003 | 10 | 1571577 | C | Unknown | G | 8 |
| S26 | 10 | 1671385 | G | T | T | 1 |
| S27 | 10 | 1671446 | A | G | G | 2 |
| S24-1 | 10 | 1671781 | C | C | T | 3 |
| S24-2 | 10 | 1671782 | C | C | T | 3 |
| S24-3 | 10 | 1671783 | G | G | C | 3 |
| S20-1 | 10 | Approx. 1671784 | C | T | NA | 4 |
| S20-2 | 10 | Approx. 1671785 | T | G | NA | 4 |
| S20-3 | 10 | Approx. 1671788 | T | C | NA | 4 |
| S28-1 | 10 | 1687167 | C | T | T | 5 |
| S28-2 | 10 | 1687168 | A | G | G | 5 |
| S28-3 | 10 | 1687182 | T | A | A | 5 |
| S28-4 | 10 | 1687183 | C | T | T | 5 |
| S28-5 | 10 | 1687184 | A | G | G | 5 |
| S28-6 | 10 | 1687185 | A | G | G | 5 |
| SNP004 | 10 | 1587437 | G | Unknown | A | 9 |
| SNP005 | 10 | 1782123 | A | G | G | 10 |
| SNP006 | 10 | 1787806 | A | T | T | 11 |

*NA—no amplification product

TABLE 4

| RppK Sequences | |
|---|---|
| SEQ ID NO: | Description of SEQ ID NO: |
| 12 | RppK Genomic Region |
| 13 | RppK CDS |
| 14 | RppK Amino Acid Sequence |

Example 2. K22 BAC Library Screening and Candidate Gene Identification

A BAC library from resistant line K22 was constructed according to Luo and Wing (2003). Briefly, Etiolated seedlings, growing in the dark for 2-3 weeks, were collected and frozen in liquid nitrogen. A total of 120,960 clones were obtained in the vector pIndigoBAC536-S with enzyme HindIII. Single clones in 315 384-plates with an average insert size of 150 Kb. Primer pairs for RUST7-5, RUSTS-2 and RUSTS-4 (low-copy sequences within the QTL interval) were used to screen the K22 BAC library. Five overlapping BAC clones were identified and sequenced with PacBio RSII. The Five BAC clones cover a contiguous 280 kb region, and the closest flanking markers (SNP20 and SNP5) are 21 kb apart. There are three annotated NLR (nucleotide binding, leucine-rich repeat) genes, R1, R2 and R3, within this interval. R1 was subsequently excluded through further mapping analysis. The expression level of R2 in leaves is below detection level, while R3 is expressed in leaves, making R3 (SEQ ID NO: 14) a leading candidate for RppK.

Example 3. Transgenic Validation of R3 as the Causal Gene for RppK

Genomic sequence of the R3 gene (including the promoter region) was synthesized and cloned into a binary vector for transformation in HC69. Single copy quality events were crossed to HC69 to generate segregating T1 seeds. T1 plants were inoculated with the *Puccinia polysora* urediospores and kept in the greenhouse for 10 days. Greenhouse disease scoring was done visually as susceptible (S) or resistant (R) based on presence or absence of erupted uredia (a sporulating postule), respectively. In total 30 T1 plants with a single copy of transgene and 20 T1 plants without the transgene, all from the same 6 events, were test for SCR resistance in the greenhouse. All the 30 transgene positive plants gave the resistant phenotype, while all the transgene negative plants were scored as susceptible. It is concluded that the R3 gene confers resistance to SCR and is the causal gene for RppK.

What is claimed:

1. A method of increasing resistance to southern corn rust in a maize plant, comprising expressing in a maize plant a recombinant polynucleotide that (i) comprises a nucleic acid that encodes a polypeptide having an amino acid sequence of at least 95% sequence identity to the amino acid sequence set forth in SEQ ID NO:14 operably linked to a heterologous promoter; or (ii) comprises SEQ ID NO:13 operably linked to heterologous promoter; or (iii) comprises RppK genomic sequence encoding SEQ ID NO: 14 operably linked to its native promoter sequence; or (iv) comprises SEQ ID NO:12; wherein the recombinant polynucleotide provides increased resistance to southern corn rust in the maize plant when compared to a control maize plant not comprising the recombinant polynucleotide.

2. The method of claim 1, wherein the recombinant polynucleotide comprises a heterologous promoter.

3. The method of claim 1, further comprising obtaining a maize progeny plant derived from the plant expressing the recombinant polynucleotide, wherein said maize progeny plant comprises in its genome the recombinant polynucleotide and exhibits increased resistance to southern corn rust when compared to a control maize plant not comprising the recombinant polynucleotide.

4. A recombinant DNA construct comprising a polynucleotide operably linked to a heterologous promoter wherein said polynucleotide comprises a sequence encoding an amino acid sequence of at least 95% sequence identity to the amino acid sequence set forth in SEQ ID NO: 14.

5. A maize plant cell comprising the recombinant polynucleotide of claim 1.

6. A maize plant comprising the plant cell of claim 5.

7. A maize seed produced from the plant of claim 6, wherein the seed comprises the recombinant polynucleotide.

8. The method of claim 1, wherein the polynucleotide comprises a sequence having at least 95% sequence identity to SEQ ID NO:13.

9. The method of claim 1, wherein the polynucleotide comprises SEQ ID NO:13.

10. The method of claim 1, wherein the polynucleotide comprises a sequence having at least 95% sequence identity to SEQ ID NO:12.

11. The method of claim 1, wherein the polynucleotide comprises SEQ ID NO:12.

12. The maize plant of claim 6 comprising SEQ ID NO: 12.

* * * * *